US008822698B2

(12) United States Patent
Maina et al.

(10) Patent No.: US 8,822,698 B2
(45) Date of Patent: Sep. 2, 2014

(54) AMINOACID DERIVATIVES, THEIR PROCESS OF PREPARATION AND THEIR THERAPEUTICAL USES AS INHIBITORS OF ONCOGENIC SIGNALS BY THE MET FAMILY

(71) Applicants: Universite D'Aix-Marseille, Marseille (FR); Universite De Lorraine, Nancy Cedex (FR); Oreste Piccolo Studio Di Consulenza Scientifica, Sirtori (IT); Universitat De Barcelona, Barcelona (ES); Centre National De La Recherche Scientifique (C.N.R.S), Paris (FR)

(72) Inventors: Flavio Maina, Cassis (FR); Rosanna Dono, Cassis (FR); Oreste Piccolo, Sirtori (IT); Daniele Passarella, Abbiategrasso (IT); Francesco Colombo, Como (IT); Joan Bosch, Barcelona (ES); Bernard Maigret, Heillecourt (FR); Vincent Leroux, Marcoussis (FR)

(73) Assignees: Universite d'Aix-Marseille, Marseille (FR); Universite de Lorraine, Nancy (FR); Oreste Piccolo Studio di Consulenza Scientifica, Sirtori (LC) (IT); Universitat de Barcelona, Barcelona (ES); Centre National de la Recherche Scientifique (C.N.R.S.), Paris (FR)

( * ) Notice: Subject to any disclaimer, the term of this patent is extended or adjusted under 35 U.S.C. 154(b) by 0 days.

(21) Appl. No.: 13/686,985

(22) Filed: Nov. 28, 2012

(65) Prior Publication Data

US 2013/0085143 A1 Apr. 4, 2013

Related U.S. Application Data

(63) Continuation-in-part of application No. 13/498,679, filed as application No. PCT/EP2010/064332 on Sep. 28, 2010, now abandoned.

(30) Foreign Application Priority Data

Sep. 28, 2009 (EP) .................................. 09305902

(51) Int. Cl.
- C07D 513/04 (2006.01)
- A61K 31/429 (2006.01)
- A61K 31/496 (2006.01)
- A61K 31/5377 (2006.01)

(52) U.S. Cl.
CPC .................................. C07D 513/04 (2013.01)
USPC ........ 548/151; 544/133; 544/368; 514/233.2; 514/366

(58) Field of Classification Search
USPC ......................................................... 548/151
See application file for complete search history.

(56) References Cited

U.S. PATENT DOCUMENTS 5,919,799 A * 7/1999 Tasaka et al. ................. 514/322

FOREIGN PATENT DOCUMENTS

| FR | 2910895 A1 * | 7/2008 |
| WO | 2007009120 A2 | 1/2007 |

OTHER PUBLICATIONS

A machine translation of FR 2910895, 2008.*
Golub et al., Science, vol. 286, Oct. 15, 1999, pp. 531-537.*
International Search Report, dated Jan. 17, 2011, in corresponding Application No. PCT/EP2010/064332.
Salvatore Patane et al., "A new Met inhibitory-scaffold identified by a focused forward chemical biological screen", Biochemical and Biophysical Research Communications, Oct. 17, 2008, pp. 184-189, vol. 375, No. 2.
Cui, Jingrong Jean, "Inhibitors targeting hepatocyte growth factor receptor and their potential therapeutic applications", Expert Opin. Ther. Patents, 2007, vol. 17, No. 9, pp. 1035-1045.

* cited by examiner

*Primary Examiner* — Laura L. Stockton
(74) *Attorney, Agent, or Firm* — Young & Thompson

(57) ABSTRACT

Novel amino acids derivatives, in particular some amino acid amides derivatives, their process of preparation and their use for inhibiting Met-triggered disorders, in particular cancer.

19 Claims, 3 Drawing Sheets

AMINOACID DERIVATIVES, THEIR PROCESS OF PREPARATION AND THEIR THERAPEUTICAL USES AS INHIBITORS OF ONCOGENIC SIGNALS BY THE MET FAMILY

CROSS-REFERENCE

The present application is a continuation-in-part application of U.S. application Ser. No. 13/498,679, filed Mar. 28, 2012, now abandoned, which was a National Phase Application of International Application PCT/EP2010/064332, filed Sep. 28, 2010, which claimed priority to European Application EP 09305902.0, filed Sep. 28, 2009.

The present invention is related to novel aminoacids derivatives, pharmaceutical compositions comprising the same, processes for the preparation of said derivatives and uses of said compositions. Particularly, the present invention relates to pharmaceutical compositions that include some aminoacid amides derivatives and their use in the treatment or the prevention of Met-triggered or Met-related disorders, such as cancers, *Listeria* infection (see Cossart, P. (2001) *Trends Microbiol* 9, 105-107 and Veiga, E. et al. (2007). *Cell* 130, 218-219) and disease related to the Met family member Ron. Moreover, it was also reported that Met was present in DRG neurons (Maina et al., *Genes Dev* 11, 3341-3350, 1997) and it regulates identity acquisition of a subpopulation of sensory neurons (*J. Neuroscience* 15; 30(37):12414-12423, 2010), thus suggesting that Met could be involved in the sensation of pain.

BACKGROUND OF THE INVENTION

Cancer treatment is evolving from the empirical administration of chemotherapeutics to the precise deployment of molecularly targeted agents. Targeted therapies that inhibit receptor tyrosine kinases (RTKs) and their downstream signals have shown promising anticancer activity. However, their efficacy in some solid tumours has been modest and/or limited for tumour resistance developed by cancer cells. The Met RTK and its ligand, hepatocyte growth factor/scatter factor (HGF/SF), have become leading candidates for targeted cancer therapies. Inappropriate Met signalling through autocrine, paracrine, amplification, and mutational activation occurs in virtually all types of solid tumours, contributing to one or a combination of proliferative, invasive, survival, or angiogenic cancer phenotypes. Met participate in all stages of malignant progression and represent promising drug targets in a variety of cancer types, including carcinomas, sarcomas, and brain tumours. The key role of Met in cancer has been further elucidated by uncovering its properties to confer resistance to other RTK inhibitors used for therapies. In particular, Met elicits signalling rewiring through "RTK swapping" by substituting ErbBs function, thus conferring resistance to anticancer ErbBs antagonists. For these reasons, Met can be considered as a "nodal signal" not only in cancer malignancy, but also in resistance to therapies. Therefore, agents able to antagonise oncogenic Met are expected to have strong impact in targeted anticancer molecular therapies to impair Met action during tumour formation, aggressiveness acquisition and resistance to therapy.

The absolute requirement for Met under specific physiological and pathological conditions supports the concept that signalling by Met has unique functions in some cancer cells and that inhibiting Met signalling will be particularly effective for therapies of metastatic and/or resistant cancers.

Over the last years, major efforts have been made to identify Met chemical inhibitors containing a large variety of chemical structures [see Cui, J. J. (2007) *Expert. Opin. Ther. Patents* 17, 1035-1045] and some candidates are currently under clinical evaluation. Many patents and patent applications (more than 80 only in the last 5 years) as well as scientific papers have been published, thus evidencing the relevance of the problem and also the difficulty to find suitable candidates. However, none of these prior art documents disclose compounds having the structure of the compounds of the invention. In particular, Patané et al., [(2008) *Biochemical and Biophysical Research Communications* 375 (2008) 184-189] disclosed closely related Met-inhibitors. However, the disclosed compounds exhibit in vitro activity in the micromolar range and/or toxicity levels which may prove to be unsufficient.

Close structures have also been published, although not with the disclosure of any c-Met activity. In particular, WO07109120 discloses 4[(imidazo[2,1-b]benzothiazol-2-yl)aniline derivatives, but such derivatives exhibit a specific side chain comprising the —NH—C(=O)—NH— fragment, do not exemplify any amino acid derivative contrary to the compounds of the invention, are specifically active against FLT3, KIT, CSF1R and no information on a possible activity against c-Met is given.

It is thus mandatory to identify new leitmotivs to maximise target inhibition, circumvent resistance acquisition, such as resistance induced by Erbs antagonists, or to improve existing scaffolds either by modelling or by empirical attempts. Moreover, a relatively simple and industrially scalable synthesis is a pre-requisite.

Crystallographic studies have demonstrated that some Met inhibitors, such as "SU11274" [(3Z)—N-(3-Chlorophenyl)-3-({3,5-dimethyl-4-[(4-methylpiperazin-1-yl)carbonyl]-1H-pyrrol-2-yl}methylene)-N-methyl-2-oxo-2,3-dihydro-1H-indole-5-sulfonamide] and "AM7" [(5-(3-fluoro-4-((6-(methyloxy)-7-((3-(4morpholinyl)propyl)oxy)-4-quinolinyl)oxy)phenyl)-3-methyl-2-(phenylmethyl)-4(3H)-pyrimidinone)], interact within the ATP binding pocket of Met in a distinct manner. This seems to correlate with their differential abilities to inhibit oncogenic mutant forms of Met found in some tumours versus the wild-type form. Thus, Met antagonists, by binding to the receptor in a drastically different manner, can differentially impair activity of Met wild type, oncogenic germ line mutants or with somatic mutations acquired during resistance to treatment. It is suspected that combined treatment with Met inhibitors may be required to successfully shot most of the cancers. However, it is believed that none of the above Met inhibitors have a dual mechanism of action towards Met: impairing Met and downstream signalling.

It is then highly desirable to provide Met inhibitors that: 1) impair Met phosphorylation/activity, 2) act also on signalling downstream of RTKs, 3) counteract other RTKs, such as ErbBs and/or PDGFRs, that together with Met ensure signaling rewiring through RTK swapping, and/or 4) elicit an inhibitory activity at nanomolecular concentration, with a view to treat and/or prevent various forms of cancers or other Met-related diseases. Such agents could be also effective on some type of leukemia characterized by deregulated forms of the Met-related Ron RTK.

SUMMARY OF THE INVENTION

It has now been found that novel compounds of formula (I) are effective as Met inhibitors and overcome the limits of the state of art.

According to a first object, the present invention concerns compounds of formula (I):

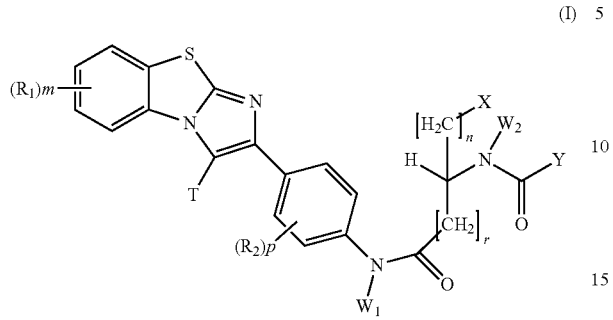

(I)

wherein:
m is an integer chosen from 0, 1, 2, 3 and 4;
p is an integer chosen from 0, 1, 2, 3 and 4;
each $R_1$, identical or different, is independently chosen from halogen atoms or a group chosen from alkyl, cycloalkyl, COOR, perhalogenoalkyl, CN, NRR', aryl, heteroaryl, -alkylaryl, -alkylheterocyclyl, $S(O)_qR$, OH, Oalkyl where alkyl is optionally substituted by one or more identical or different substituents independently chosen from halogen atom, OR, or NRR', non aromatic heterocycle;
each $R_2$, identical or different, is independently chosen from halogen atoms, alkyl, cycloalkyl, COOR, perhalogenoalkyl, CN, NRR', aryl, heteroaryl, -alkylaryl, -alkylheterocyclyl, $S(O)_qR$, OH, Oalkyl, optionally substituted by one or more identical or different substituents independently chosen from halogen atom, OR, or NRR';
T is a hydrogen or a halogen atom;
n is an integer chosen from 0, 1 and 2, where, when n is 0, the carbon atom is absent;
r is an integer chosen from 0 and 1, where, when r is 0, the carbon atom is absent;
$W_1$ is a hydrogen atom or an alkyl, aryl, -alkylaryl;
$W_2$ is a hydrogen atom or an alkyl, -alkylaryl;
X is H, an alkyl, cycloalkyl, aryl, -alkylaryl or heteroaryl, each being optionally substituted by one or more identical or different groups, independently chosen from OR, COOR, NRR', halogen atom, $S(O)_qR$, alkyl, aryl, CN, perhalogenoalkyl;
Y is an alkyl, cycloalkyl, aryl, -alkylaryl, -alkylheterocyclyl, heteroaryl, each being optionally substituted by one or more identical or different substituents independently chosen from halogen atom, OR, COOR, NRR', CN, $S(O)_qR$, alkyl, aryl, perhalogenoalkyl;
q is an integer chosen from 0, 1 or 2;
R and R', identical or different, independently represent a H atom, alkyl, aryl, -alkylaryl or R and R' together form with the N atom to which they are attached a heteroaryl or heterocyclic ring;
wherein, unless specified, the alkyl, aryl, -alkylaryl, heteroaryl, heterocyclic ring are optionally substituted by one or more of halogen atom, OH, COOR, OAlkyl, OAryl, OAlkylaryl, $NH_2$, NHAlkyl, $NAlkyl_2$, NHAryl, $NAryl_2$, NHAlkylaryl, $NAlkylaryl_2$, N(Alkyl)alkylaryl, CN, perhalogenoalkyl, SH, SAlkyl, SOAlkyl, $SO_2$alkyl, aryl, alkylaryl;
either as racemic mixtures or pure or enantioenriched enantiomers, and pharmaceutically acceptable salts thereof.

Preferred compounds of formula (I) are of formula (Ia):

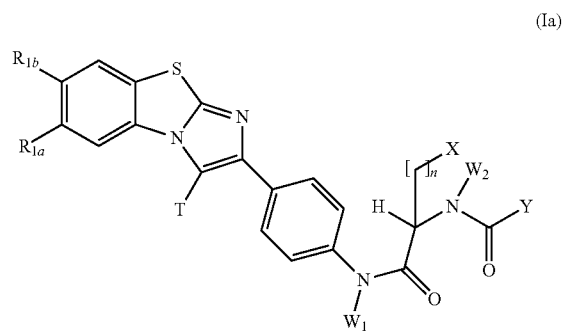

(Ia)

wherein:
$R_{1a}$ and $R_{1b}$ identical or different are independently chosen from hydrogen or halogen atoms or a group chosen from perhalogenoalkyl, CN, NRR', aryl, alkyl, OH or Oalkyl where alkyl is is optionally substituted with one or more identical or different substituents independently chosen from halogen atom, OR, NRR', non aromatic heterocycle, such as morpholinyl;
T is a hydrogen or a halogen atom;
n is an integer chosen from 0 and 1, where, when n is 0, the carbon atom is absent;
$W_1$ and $W_2$, identical or different, are chosen from a hydrogen atom or a $C_{1-4}$ alkyl;
X is H, an alkyl, an aryl or heteroaryl, each being optionally substituted by one or more identical or different groups, independently chosen from OR, COOR, NRR', halogen atom, $S(O)_qR$, alkyl, aryl, CN, perhalogenoalkyl;
Y is an alkyl, aryl, -alkylaryl such as $—CH_2$aryl, heteroaryl, each being optionally substituted by one or more identical or different substituents independently chosen from halogen atom, OR, COOR, NRR', CN, $S(O)_qR$, alkyl, aryl, perhalogenoalkyl;
q is an integer chosen from 0, 1 or 2;
R and R', identical or different, independently represent a hydrogen atom, alkyl, aryl, alkylaryl or R and R' together form with the N atom to which they are attached a heterocyclic ring;
wherein the alkyl, aryl, -alkylaryl, heterocyclic ring are optionally substituted by one or more of halogen atom, OH, OAlkyl, OAryl, OAlkylaryl, $NH_2$, NHAlkyl, $NAlkyl_2$, NHAryl, $NAryl_2$, NHAlkylaryl, NAlkylaryl, $NAlkylaryl_2$, N(Alkyl)alkylaryl, CN, perhalogenoalkyl, SH, SAlkyl, SOAlkyl, $SO_2$alkyl, aryl, alkylaryl;
either as racemic mixture or pure or enantioenriched enantiomers, as well as the pharmaceutically acceptable salts thereof.

More preferred compounds are those of formula (Ia) as defined above, in which X is an aryl or heteroaryl, each being optionally substituted by one or more identical or different groups, independently chosen from OR, COOR, NRR', halogen atom, $S(O)_qR$, alkyl, aryl, CN, perhalogenoalkyl.

The present invention also encompasses the following preferred embodiments of formulae (I) or (Ia) or any of their combination:
m=0 or 1, p=0, r=0 and T=H; and/or
$W_1=W_2=H$; and/or
n=0 or 1; and/or
X is an optionally substituted aryl or heteroaryl; and/or
X is a phenyl; and/or at least one of $R_{1a}$ and $R_{1b}$ is H; and/or Y is an -alkylaryl, such as —CH$_2$aryl, where the aryl, such as phenyl, is optionally substituted, preferably substituted by one or more identical or different substituents chosen from halogen, OR, NRR', SR, alkyl, CN, perhalogenoalkyl.

More preferred compounds of formula (I) are of formula (Ib):

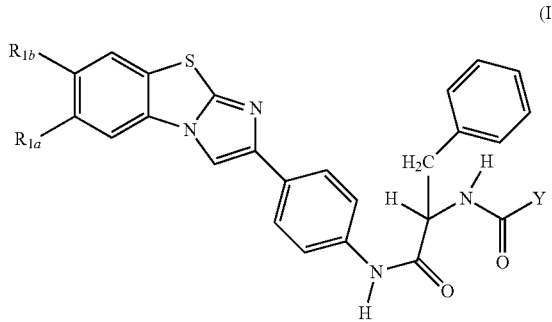

(Ib)

wherein:
- Y is an -alkylaryl, such as —CH$_2$aryl, where aryl is a phenyl optionally substituted, preferably substituted, by one or more identical or different substituents independently chosen from halogen atom, preferentially fluorine atom, an alkyl group, preferentially methyl group, a perhalogenoalkyl group, preferentially trifluoromethyl group;
- One of $R_{1a}$ and $R_{1b}$ is H and the other, identical or different, is independently chosen from hydrogen or halogen atoms or Oalkyl where alkyl is is optionally substituted with one or more identical or different substituents independently chosen from halogen atom, OR, NRR', non aromatic heterocycle, such as morpholinyl; preferably both $R_{1a}$ and $R_{1b}$ are H;

either as racemic mixture or pure or enantioenriched enantiomers, as well as the pharmaceutically acceptable salts thereof.

According to a preferred aspect, the compounds of the invention are selected from the group consisting in:
2-(3,5-dimethylphenylacetamido)-3-phenyl-N-[4-(imidazo[2,1-b]benzothiazol-2-yl)phenyl]propanamide;
2-(3,5-dimethylphenylacetamido)-3-(4-hydroxyphenyl)-N-[4-(imidazo[2,1-b]benzo thiazol-2-yl)phenyl]propanamide;
2[(3,5-bis(trifluoromethyl)phenylacetamido)-3-phenyl-N-[4-(imidazo[2,1-b]benzo thiazol-2-yl)phenyl]propanamide;
2[(3,5-difluorophenylacetamido)-3-phenyl-N-[4-(imidazo[2,1-b]benzothiazol-2-yl)phenyl]propanamide;
2[(3,5-bis(trifluoromethyl)phenylacetamido)-N-[4-(imidazo[2,1-b]benzothiazol-2-yl)phenyl]propanamide;
2[(3,5-difluorophenylacetamido)-N-[4-(imidazo[2,1-b]benzothiazol-2-yl)phenyl]propanamide;
2-(3,5-dimethylphenylacetamido)-N-[4-(imidazo[2,1-b]benzothiazol-2-yl)phenyl]propanamide;
2-(3,5-dimethylphenylacetamido)-N-[4-(imidazo[2,1-b]benzothiazol-2-yl)phenyl]acetamide;
2-(3,5-dimethylphenylacetamido)-3-(3-indolyl)-N-[4-(imidazo[2,1-b]benzothiazol-2-yl)phenyl]propanamide;
2-[(3,5-bis(trifluoromethyl)phenylacetamido)-3-(3-indolyl)-N-[4-(imidazo[2,1-b]benzothiazol-2-yl)phenyl]propanamide;
2-[(3,5-bis(trifluoromethyl)phenylacetamido)-3-(2-naphthyl)-N-[4-(imidazo[2,1-b]benzothiazol-2-yl)phenyl]propanamide;
2-(3,5-dimethylphenylacetamido)-3-(2-naphthyl)-N-[4-(imidazo[2,1-b]benzothiazol-2-yl)phenyl]propanamide;
2-(3,5-dimethylphenylacetamido)-N-[4-(imidazo[2,1-b]benzothiazol-2-yl)phenyl]phenylacetamide;
2-(3,5-dimethylphenylacetamido)-3-(hydroxyl)-N-[4-(imidazo[2,1-b]benzothiazol-2-yl)phenyl]propanamide;
2[(3,5-bis(trifluoromethyl)phenylacetamido)-3-phenyl-N-[4-(imidazo[2,1-b](6-methoxy)benzo thiazol-2-yl)phenyl]propanamide;
2[(3,5-bis(trifluoromethyl)phenylacetamido)-3-phenyl-N-[4-(imidazo[2,1-b](6-(3-(dimethylamino)propoxy)benzo thiazol-2-yl)phenyl]propanamide;
2[(3,5-bis(trifluoromethyl)phenylacetamido)-3-phenyl-N-[4-(imidazo[2,1-b](6-(3-(hydroxy)propoxy)benzo thiazol-2-yl)phenyl]propanamide;
2-(3,5-dimethylphenylacetamido)-N-[4-(imidazo[2,1-b](6-(3-(hydroxy)propoxy)benzothiazol-2-yl)phenyl]phenylacetamide;
2-(3,5-dimethylphenylacetamido)-N-[4-(imidazo[2,1-b](6-(3-(1-piperazinyl)propoxy)benzothiazol-2-yl)phenyl]phenylacetamide;
(S)-2-(3,5-bis(trifluoromethyl)phenylacetamido)-3-phenyl-N-[4-(7-bromo)imidazo[2,1-b]benzothiazol-2-yl)phenyl]propanamide
(S)-2-(4-methylphenylacetamido)-3-phenyl-N-[4-(imidazo[2,1-b]benzothiazol-2-yl)phenyl]propanamide
(S)-2-(3,5-dimethyl)phenylacetamido)-3-(4-methylphenyl)-N-[4-(imidazo[2,1-b]benzothiazol-2-yl)phenyl]propanamide
(S)-2-(3,5-bis(trifluoromethyl)phenylacetamido)-3-(4-methylphenyl)-N-[4-(imidazo[2,1-b]benzothiazol-2-yl)phenyl]propanamide
(S)-2-(3,5-dimethylphenylacetamido)-3-(1H-indol-3-yl)-N-[4-(imidazo[2,1-b]benzothiazol-2-yl)phenyl]propanamide
(S)-2-(3,5-bis(trifluoromethylphenylacetamido)-3-(1H-indol-3-yl)-N-[4-(imidazo[2,1-b]benzothiazol -2-yl)phenyl]propanamide
(S)-2-(3,5-dimethylphenylacetamido)-3-phenyl-N-[4-(7-(2-morpholin-4-yl-ethoxy)imidazo[2,1-b]benzothiazol-2-yl)phenyl]propanamide
(S)-2-(3,5-bis(trifluoromethyl)phenylacetamido)-3-phenyl-N-[4-(7-(2-morpholin-4-yl-ethoxy)imidazo[2,1-b]benzothiazol-2-yl)phenyl]propanamide
(S)-2-(3,5-dimethylphenylacetamido)-3-phenyl-N-[4-(6-(2-morpholin-4-yl-ethoxy)imidazo[2,1-b]benzothiazol-2-yl)phenyl]propanamide or their racemic mixtures or pure or enantioenriched enantiomers, and pharmaceutically acceptable salts thereof.

More preferably, the compounds of the invention are chosen from:
(S)-2-(3,5-dimethylphenylacetamido)-3-phenyl-N-[4-(imidazo[2,1-b]benzothiazol-2-yl)phenyl]propanamide;
(R)-2-(3,5-dimethylphenylacetamido)-3-phenyl-N-[4-(imidazo[2,1-b]benzothiazol-2-yl)phenyl]propanamide;
(S)-2[(3,5-bis(trifluoromethyl)phenylacetamido)-3-phenyl-N-[4-(imidazo[2,1-b]benzothiazol-2-yl)phenyl]propanamide;
(R)-2[(3,5-bis(trifluoromethyl)phenylacetamido)-3-phenyl-N-[4-(imidazo[2,1-b]benzothiazol-2-yl)phenyl]propanamide
(S)-2[(3,5-difluorophenylacetamido)-3-phenyl-N-[4-(imidazo[2,1-b]benzothiazol-2-yl)phenyl]propanamide;

(R)-2[(3,5-difluorophenylacetamido)-3-phenyl-N-[4-(imidazo[2,1-b]benzothiazol-2-yl)phenyl]propanamide;

(S)-2-(3,5-bis(trifluoromethyl)phenylacetamido)-3-phenyl-N-[4-(7-bromo)imidazo[2,1-b]benzothiazol-2-yl)phenyl]propanamide (S)-2-(4-methylphenylacetamido)-3-phenyl-N-[4-(imidazo[2,1-b]benzothiazol-2-yl)phenyl]propanamide as well as their pharmaceutically acceptable salts.

As used herein, the term "alkyl" refers to a branched or straight hydrocarbon chain of 1 to 8 carbon atoms, which is formed by the removal of one hydrogen atom. preferably from 1 to 6 carbon atoms. Examples include methyl, ethyl, n-propyl, isopropyl, n-butyl, isobutyl, sec-butyl, t-butyl, pentyl, 2-methylpentyl, hexyl, 2-methylhexyl, 2,3-dimethylhexyl, heptyl, octyl, etc.

As used herein, the term "cycloalkyl" refers to a non aromatic hydrocarbon mono, bi or multi cyclic ring of 3 to 10 carbon atoms formed by the removal of one hydrogen atom. Examples include cyclopropyl, cyclopentyl, cyclohexyl, cycloheptyl, adamantyl, etc. as well as the systems formed by their condensation such as decalinyl or by the condensation with a phenyl group such as tetralinyl. A designation such as "$C_5$-$C_7$ cycloalkyl" refers to a cycloalkyl radical containing from 5 to 7 carbon atoms.

As used herein, the term "aromatic" or "aryl" refers to a carbocyclic system as defined herein, which satisfies the Hückel (4n+2) rule and/or with a stability due to delocalization significantly greater than that of a hypothetic localized structure.

As used herein, the terms "heterocycle" or "heterocyclic" refer to a saturated, an unsaturated or a partially unsaturated 3 to 14, preferably 5 to 10 membered mono- or bi-cyclic rings wherein at least one member of the ring is a hetero atom. When the heterocycle is aromatic according to the Hückel (4n+2) rule the term heteroaryl is used. Typically, heteroatoms include, but are not limited to, oxygen, nitrogen, sulfur, selenium, and phosphorus atoms. Preferable heteroatoms are oxygen, nitrogen and sulfur. The nitrogen and sulfur heteroatoms may be optionally oxidized, and the nitrogen may be optionally substituted in non-aromatic rings. The bonds connecting the endocyclic atoms of a heterocyclic group may be single, double, triple, or part of a fused aromatic moiety.

Heterocycles are intended to include non aromatic heterocyclic ("heterocyclyl") and aromatic heterocyclic ("heteroaryl") compounds.

Examples of heterocycles include, but are not limited to oxiranyl, aziridinyl, tetrahydrofuranyl, 1,2-dioxolanyl, 1,3-dioxolanyl, 1,4-dioxolanyl, tetrahydro-pyranyl, 1,2-dioxanyl, 1,3-dioxanyl, 1,4-dioxanyl, tetrahydro-thiophenyl, tetrahydrothiopyran, 1,2-di-thiolanyl, 1,3-dithiolanyl, 1,2-dithianyl, 1,3-dithianyl, 1,4-dithianyl, tetrahydrothiopyranyl, thiomorpholinyl, thiazolidinyl, oxiranyl, pyrrolidinyl, 2-pyrrolidinyl, pirazolidinyl, piperidyl, 4-piperidinyl, morpholino, morpholinyl, piperazinyl, imidazolidinyl, pyranyl, dihydrofuranyl, dihydropyranyl, imidazolinyl, pyrrolinyl, pirazolinyl, tetrahydropyridyl, dihydropyridyl, tetrahydropyrimidinyl, dihydrothiophenyl, dihydrothiopyranyl, furanyl, pyrrolyl, 2H-pyrrolyl, imidazolyl, pyrazolyl, thienyl, oxadiazolyl, 1,2,3-oxadiazolyl, 1,2,4-oxadiazolyl, 1,2,5-oxadiazolyl, 1,3,4-oxadiazolyl, oxazolyl, isoxazolyl, furazanyl, 1,2,3-thiadiazolyl, 1,2,4-thiadiazolyl, 1,2,5-thiadiazolyl, 1,3,4-thiadiazolyl, thiazolyl, isothiazolyl, pyridyl, pyrazinyl, pyrimidinyl, pyridazinyl, indolizinyl, indolyl, indazolyl, purinyl, quinolizinyl, quinolyl, isoquinolyl, phthalazinyl, naphthyridinyl, quinoxalinyl, quinazolinyl, cinnolinyl, pteridinyl, oxazolinyl, 6H-1,2,5-thiadiazinyl, 2H,6H-1,5,2-dithiazinyl, oxazolidinyl, piperidonyl, 6H-1,2,5-thiadiazinyl, thienothiazolyl, thienooxazolyl, thienoimidazolyl, triazinyl, 1,2,3-triazolyl, 1,2,4-triazolyl, 1,2,5-triazolyl, 1,3,4-triazolyl, and tetrazole, as well as the systems formed by their condensation or the condensation with a phenyl group. Suitable heterocycles are also disclosed in *The Handbook of Chemistry and Physics,* 76th Edition, CRC Press, Inc., 1995-1996, pages 2-25 to 2-26, the disclosure of which is hereby incorporated by reference.

Preferred heterocyclic groups formed with a nitrogen atom include, but are not limited to, pyrrolidinyl, pyrrolyl, pirazolyl, pirazolidinyl, piperazinyl, imidazolidinyl, pyrrolinyl, pirazolinyl, pyridyl, piperidyl, piperidino, morpholinyl, morpholino, thiomorpholino, N-methylpiperazinyl, indolyl, isoindolyl, imidazolyl, imidazolinyl, oxazoline, oxazole, triazole, thiazoline, thiazole, isothiazole, thiadiazoles, triazines, isoxazole, oxindole, indoxyl, pyrazole, pyrazolone, pyrimidine, pyrazine, quinoline, iosquinoline, and tetrazole groups.

Preferred heterocyclic groups formed with an oxygen atom include, but are not limited to, furan, tetrahydrofuran, pyran, benzofurans, isobenzofurans, and tetrahydropyran groups.

Preferred heterocyclic groups formed with a sulfur atom include, but are not limited to, thiophene, thianaphthene, tetrahydrothiophene, tetrahydrothiapyran, and benzothiophenes.

As used herein, the term "aryl" refers to an aromatic carbo, mono-, bi-or multicyclic hydrocarbon ring containing from 6 to 14, preferably 6 to 10 carbon atoms, which is formed by removal of one hydrogen atom. Examples include phenyl, naphthyl, etc.

As used herein, "Hal" refers to a halogen atom, including fluoro, chloro, iodo, bromo.

As used herein, the term "subject" refers to a warm blooded animal such as a mammal, preferably a human, or a human child, which is afflicted with, or has the potential to be afflicted with one or more diseases and conditions described herein.

As used herein, a "therapeutically effective amount" refers to an amount of a compound of the present invention which is effective in reducing, eliminating, treating or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, "pharmaceutically acceptable salts" refer to derivatives of the disclosed compounds wherein the parent compound is modified by adding an acid thereto. The pharmaceutically acceptable salts include the conventional non-toxic salts of the parent compound formed, for example, from non-toxic inorganic or organic acids. For example, such conventional non-toxic salts include those derived from inorganic acids such as hydrochloric, sulfuric, sulfamic, phosphoric, nitric and the like; and the salts prepared from organic acids such as acetic, propionic, succinic, tartaric, citric, glutamic, glucuronic, benzoic, salicylic, toluenesulfonic, methanesulfonic, oxalic, fumaric, maleic and the like.

The pharmaceutically acceptable salts of the present invention can be synthesized from the parent compound which contains a basic moiety by conventional chemical methods. Generally, such salts can be prepared by reacting the free base forms of these compounds with a stoichiometric amount of the appropriate acid in water or in an organic solvent, or in a mixture of the two. Organic solvents like diethylether, ethyl acetate, ethanol, isopropanol, acetone, butanone or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The compounds of the general formula (I) having geometrical and stereomers are also a part of the invention.

According to a further object, the present invention is also concerned with the process of preparation of the compounds of formula (I).

The compounds and process of the present invention may be prepared in a number of ways well known to those skilled in the art. The compounds can be synthesized, for example, by application or adaptation of the methods described below, or variations thereon as appreciated by the skilled artisan. The appropriate modifications and substitutions will be readily apparent and well known or readily obtainable from the scientific literature to those skilled in the art.

In particular, such methods can be found in R. C. Larock, *Comprehensive Organic Transformations*, VCH publishers, 1989 and March's *Advanced Organic Chemistry*, V° ed, Wiley, 2001.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

Compounds of the present invention may be prepared by a variety of synthetic routes. The reagents and starting materials are commercially available, or readily synthesized by well-known techniques by one of ordinary skill in the arts. All substituents, unless otherwise indicated, are as previously defined.

In the reactions described hereinafter, it may be necessary to protect reactive functional groups, for example hydroxy, amino, imino, thio or carboxy groups, where these are desired in the final product, to avoid their unwanted participation in the reactions. Conventional protective groups may be used in accordance with standard practice, for examples see T. W. Greene and P. G. M. Wuts in *Protective Groups in Organic Chemistry*, John Wiley and Sons, 1991; J. F. W. McOmie in *Protective Groups in Organic Chemistry*, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, trialkylamines, pyridine, dimethylaminopyridine or alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, methylcyclohexane, toluene and xylenes; amides, such as N,N-dimethylformamide (DMF) and N-methyl-pyrrolidone; alcohols such as i.propanol, ethanol and methanol; halocarbons such as dichloromethane and ethers, such as diethyl ether, methyl tert-butyl ether, diisopropylether, tetrahydrofuran and 2-methyl-tetrahydrofuran; esters such as ethylacetate or butylacetate; ketones such as acetone, butanone or methyl-i.butylketone.

The reactions can take place over a wide range of temperatures. In general, we find it convenient to carry out the reaction at a temperature of from −78° C. to 200° C. (more preferably from about 0° C. to 100° C.). The time required for the reaction may also vary widely, depending on many factors, notably the reaction temperature and the nature of the reagents. However, provided that the reaction is effected under the preferred conditions outlined above, a period of up to 48 hours will usually suffice.

The compound thus prepared may be recovered from the reaction mixture by conventional means. For example, the compounds may be recovered by distilling off the solvent from the reaction mixture or, if necessary, after distilling off the solvent from the reaction mixture, pouring the residue into water followed by extraction with a water-immiscible organic solvent and distilling off the solvent from the extract or by precipitation. Additionally, the product can, if desired, be further purified by various well-known techniques, such as recrystallization, reprecipitation or the various chromatography techniques, notably column chromatography or preparative thin layer chromatography or preparative HPLC.

The compounds of formula (I) may be obtained by various pathways, as illustrated by the following three preferred representative embodiments:

According to a first aspect, compounds of the invention of the formula (I) can be obtained by reacting corresponding a compound of formula (II) with a corresponding compound of formula (III), or precursors thereof:

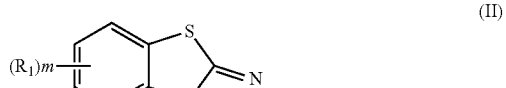

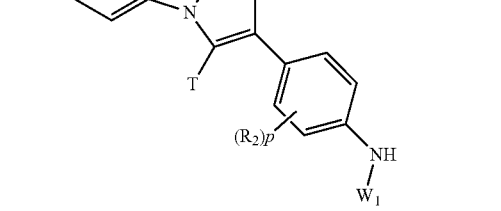

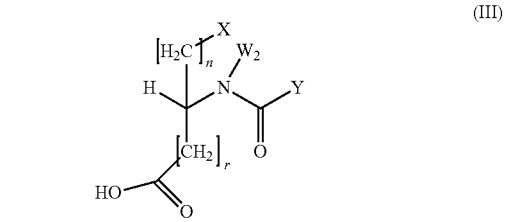

wherein $R_1, R_2, T, W, W_1, W_2, X, Y, m, n, p, r$ are defined as in formula (I).

Generally, the coupling reaction is carried out in an organic, aprotic solvent, such as dichloromethane or DMF, at room temperature, in the presence of a base such as for example triethylamine, diisopropylethylamine (DIPEA) or 4-dimethyl-aminopyridine (DMAP) and of one or more activating coupling agents, such as for example BOP-Cl [bis(2-oxo-3-oxazolidinyl)phosphinic chloride], HOBT (1-hydroxybenzotriazole), HATU [(o-7-azabenzotriazol-1-yl)-N,N,N',N'-tetramethyl uronium hexafluorophosphate], DCC (1,3-dicyclohexylcarbodiimide), 1-(3-dimethylaminopropyl)3-ethylcarbodiimide-HCl(EDC-HCl), 1,1'carbonyl-di-imidazole or 4,5-Dicyanoimidazole (DCI).

Precursor thereof is used herein to refer to compounds which differ from the indicated or desired compounds by the presence and/or absence of functions. Such functions may be introduced, transformed and/or omitted by common functionalization reactions, known from the skilled person.

The functionalization reaction may be carried out by application or adaptation of known methods.

Compounds of formula (I) may be directly obtained by reacting a compound of formula (II) with a compound of formula (XIII) and a compound of formula (XIV) where (XIII) and (XIV) react together to form in situ the compound of formula (III) (one pot reaction).

According to a second aspect, compounds of the invention of the formula (I) may be obtained by reacting a corresponding compound of formula (IV) with a corresponding compound of formula (V), or precursors thereof:

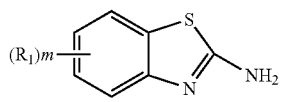

(IV)

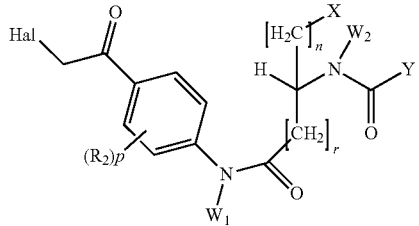

(V)

wherein $R_1, R_2, W_1, W_2, X, Y, m, n, p, r$ are defined as in formula (I) and Hal represents a halogen atom, such as Cl or Br.

Generally, the coupling reaction is carried out in a solvent, such as ethanol or i.propanol or i.butanol or 2-methoxy-ethanol, at a temperature comprised between 20° C. and 150° C. The product may be recovered by precipitation at low temperature, for example in accordance with T. Mase et al. (1986), *J. Med. Chem.* 29, 386-394).

According to a third aspect, compounds of the invention of the formula (I) may be obtained by reacting a corresponding compound of formula (VI) with a corresponding compound of formula (VII), or precursors thereof:

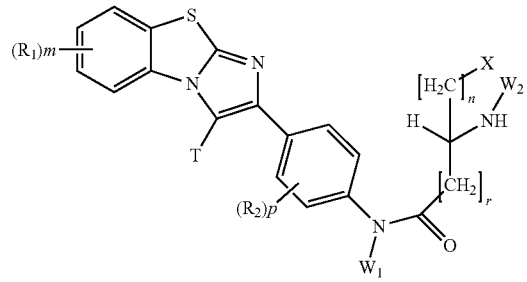

(VI)

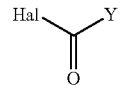

(VII)

wherein $R_1, R_2, T, W_1, W_2, X, Y, m, n, p, r$ are defined as in formula (I) and Hal represents a halogen atom, such as Cl.

Generally, the coupling reaction is carried out in a solvent, such as methylene chloride or toluene, at a temperature comprised between 0° C. and 50° C., in the presence of a base. Alternatively other well known methods to produce an amide by reaction of an amine and a carboxylic acid derivative may be used.

Said compounds of formula (II), (III), (IV), (V), (VI) or (VII) may be commercially available or may be synthesized by applying or adapting any known methods, such as those described in the examples.

More specifically, the compounds of formula (II) may be obtained by reduction of the corresponding nitro derivatives of formula (VIII):

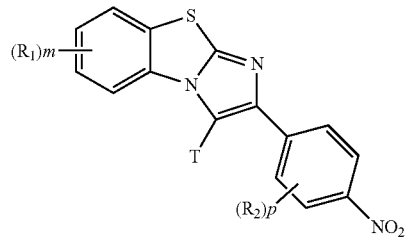

(VIII)

followed by optional substitution of H with $W_1$.

Said compound of formula (VIII) may be obtained by reacting a corresponding compound of formula (IX) with a corresponding compound of formula (X), or precursors thereof:

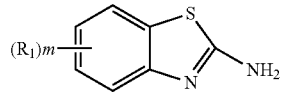

(IX)

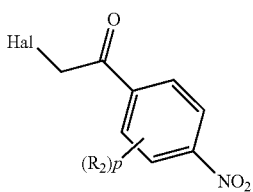

(X)

where Hal represents a halogen atom, such as Cl or Br.

The compounds of formula (VI) may be obtained by deprotecting corresponding compounds of formula (XI):

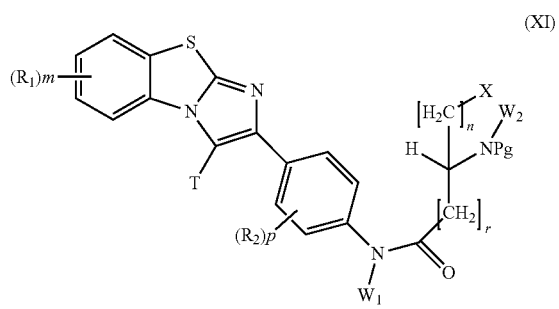

(XI)

where Pg represents an amino protective group. In turn said compounds of formula (XI) may be obtained by coupling a corresponding compound of formula (II), as defined above, with a corresponding compound of formula (XII):

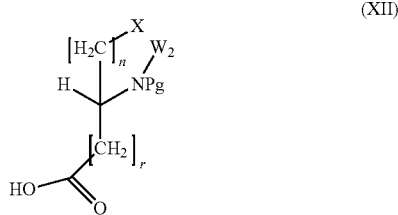

(XII)

where Pg represents said protective group.

Suitable protective groups include usual protective groups used for aminoacids such as for example "Boc" and "Fmoc", Compounds of formula (III):

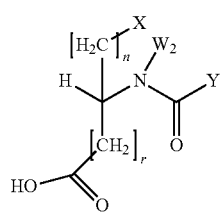

(III)

may be obtained by reacting a corresponding compound of formula (XIII):

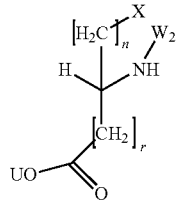

(XIII)

where U is H or an alkyl group, $W_2$, X, n, r are defined as in formula (I), optionally in the form of a salt, with a corresponding compound of formula (XIV):

(XIV)

where Y is defined as in formula (I).

The reaction may be conducted in the presence of coupling agents such as 4-dimethylaminopyridine (DMAP) and/or 1,3-diisopropylcarbodiimide (DIC); in an organic solvent such as dichloromethane. The reaction may comprise the setp of regenerating the free base of the obtained compound.

The compounds of formula (III) may be used for preparing the compounds of formula (I) in situ, without separation (one pot reaction).

The above reactions may be carried out on racemic mixtures, enriched enantiomeric mixtures or enantiomers.

Compounds of formulae (IX), (X), (XII) are commercially available or may be obtained from commercially available precursors thereof by routine methods.

The process of the invention may also comprise the additional step of isolating said desired compound of formula (I).

According to a still further aspect, the present invention also provides pharmaceutical compositions comprising at least one compound of the present invention of formula (I) and a pharmaceutically acceptable carrier, excipient or diluent.

According to a further object, the present invention also provides a compound of formula (I) for inhibiting the Met oncogene, downstream signals and/or RTKs participating to RTK swapping (e.g. ErbBs and/or PDGFRs).

According to a further object, the present invention also provides a compound of formula (I) as defined above for treating and/or preventing Met triggered disorders. Met triggered disorders refer particularly to cancers, infectious disorders and pain.

"Cancer" as used herein refers to various forms of malignant neoplasms of all organs or tissues, such as tumors or leukemia, and includes carcinoma, sarcoma, lymphoma, leukemia, germ cell tumor, blastoma, melanoma. It particularly encompasses lung including non-small cell lung cancer, breast, prostate, CNS, brain, head and neck, uterine, cervix, ovary, bladder, liver, pancreas, colorectal, colon, stomach (gastric) cancers, etc.

The present invention also concerns the corresponding methods for inhibiting integration, treating and/or preventing cancer, such as in a subject in need thereof, said method comprising administering to said subject a therapeutically effective amount of a compound of formula (I) as defined above.

The identification of those subjects who are in need of treatment of herein-described diseases and conditions is well within the ability and knowledge of one skilled in the art. A clinician skilled in the art can readily identify, by the use of clinical tests, physical examination and medical/family history, those subjects who are in need of such treatment.

A therapeutically effective amount can be readily determined by the attending diagnostician, as one skilled in the art, by the use of conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

The amount of a compound of formula (I), which is required to achieve the desired biological effect will vary depending upon a number of factors, including the dosage of the drug to be administered, the chemical characteristics (e.g., hydrophobicity) of the compounds employed, the potency of the compounds, the type of disease, the diseased state of the patient, and the route of administration.

In general terms, the compounds of this invention may be provided in an aqueous physiological buffer solution containing about 0.1 to 10% w/v compound for parenteral administration. Typical dose ranges are from about 1 µg/kg to about 1 g/kg of body weight per day; a preferred dose range is from about 0.01 mg/kg to 100 mg/kg of body weight per day. A preferred daily dose for adult humans includes about 25, 50, 100, 200 and 400 mg, and an equivalent dose in a human child. The preferred dosage of drug to be administered is likely to depend on such variables as the type and extent of progression of the disease or disorder, the overall health status of the particular patient, the relative biological efficacy of the compound selected, and formulation of the compound excipient, and its route of administration.

The compounds of the present invention are capable of being administered in unit dose forms, wherein the term "unit dose" means a single dose which is capable of being administered to a patient, and which can be readily handled and packaged, remaining as a physically and chemically stable unit dose comprising either the active compound itself, or as a pharmaceutically acceptable composition, as described hereinafter. As such, typical daily dose ranges are from about 0.01 to 100 mg/kg of body weight. By way of general guidance, unit doses for humans range from about 0.1 mg to about 1000 mg per day. Preferably the unit dose range is from about 1 to about 500 mg administered one to four times a day, and even more preferably from about 10 mg to about 300 mg, two times a day. Compounds provided herein can be formulated into pharmaceutical compositions by admixture with one or more pharmaceutically acceptable carriers, excipients or diluents. Such compositions may be prepared for use in oral administration, particularly in the form of tablets or capsules; or parenteral administration, particularly in the form of liquid solutions, suspensions or emulsions; or intranasally, particularly in the form of powders, nasal drops, or aerosols; or dermally, for example, topically or via trans-dermal patches. Controlled release formulations or targeted formulations are preferred.

The compositions may conveniently be administered in unit dosage form and may be prepared by any of the methods well known in the pharmaceutical art, for example, as described in *Remington: The Science and Practice of Pharmacy*, 20<sup>th</sup> ed.; Gennaro, A. R., Ed.; Lippincott Williams & Wilkins: Philadelphia, Pa., 2000 and/or in *Nanotechnology for cancer therapy*, Mansoor M. Amiji Ed.; CRC Press, 2007.

Pharmaceutically compatible binding agents, and/or adjuvant materials can be included as part of the composition. Oral compositions will generally include an inert diluent carrier or an edible carrier.

The tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolve, modified-release or sustained-release preparations and formulations, and wherein such sustained-release formulations are preferably bi-modal.

Preferred formulations include pharmaceutical compositions in which a compound of the present invention is formulated for oral or parenteral administration, or more preferably those in which a compound of the present invention is formulated as a tablet. Preferred tablets contain lactose, cornstarch, magnesium silicate, croscarmellose sodium, povidone, magnesium stearate, or talc in any combination. It is also an aspect of the present disclosure that a compound of the present invention may be incorporated into a food product or a liquid.

Liquid preparations for administration include sterile aqueous or nonaqueous solutions, suspensions, and emulsions. The liquid compositions may also include binders, buffers, preservatives, chelating agents, sweetening, flavoring and coloring agents, and the like. Nonaqueous solvents include alcohols, propylene glycol, polyethylene glycol, vegetable oils such as olive oil, and organic esters such as ethyl oleate. Aqueous carriers include mixtures of alcohols and water, buffered media, and saline. In particular, biocompatible, biodegradable lactide polymer, lactide/glycolide copolymer, or polyoxyethylene-polyoxypropylene copolymers or cyclodextrins or liposomes may be useful excipients to control the release of the active compounds. Intravenous vehicles can include fluid and nutrient replenishers, electrolyte replenishers, such as those based on Ringers dextrose, and the like. Other potentially useful parenteral delivery systems for these active compounds include ethylene-vinyl acetate copolymer particles, osmotic pumps, implantable infusion systems, and liposomes.

Alternative modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for buccal administration include, for example lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations. Formulations suitable for transdermal administration can be presented as discrete patches and can be lipophilic emulsions or buffered, aqueous solutions, dissolved and/or dispersed in a polymer or an adhesive.

According to another object, the compounds of the invention may also be encapsulated in suitable carriers such as cyclodextrins.

The compounds of the current invention can be employed as the sole active ingredient in a pharmaceutical composition. Alternatively, they can be used in combination or combined with other pharmaceutical agents associated with the same or other disease states. In particular, the compounds of formula (I) can be combined with agents that are useful for the treatment and/or prevention of cancer(s), infections diseases and pain, more particularly of cancer, such as topoisomerase inhibitors, anthracyclines, spindle poison plant alkaloids, alkylating agents, antimetabolites, etc. . . . Their inhibition properties on other signals either downstream of Met or parallel to Met are also encompassed. Combinations with receptor inhibitors, such as Erbs receptors inhibitors or PDGF receptors inhibitors, or with inhibitors of intracellular signaling pathways, such as inhibitors of Abl, Pl3K and/or Ras pathways, are also encompassed. The present invention encompasses, therefore, combinations of the compounds of the current invention with agents or pharmaceutical compositions known to be prescribed or effective with regard to such conditions, such as Glivec for instance.

Said ingredients can be administered simultaneously or separately.

EXAMPLES

Figure 1:
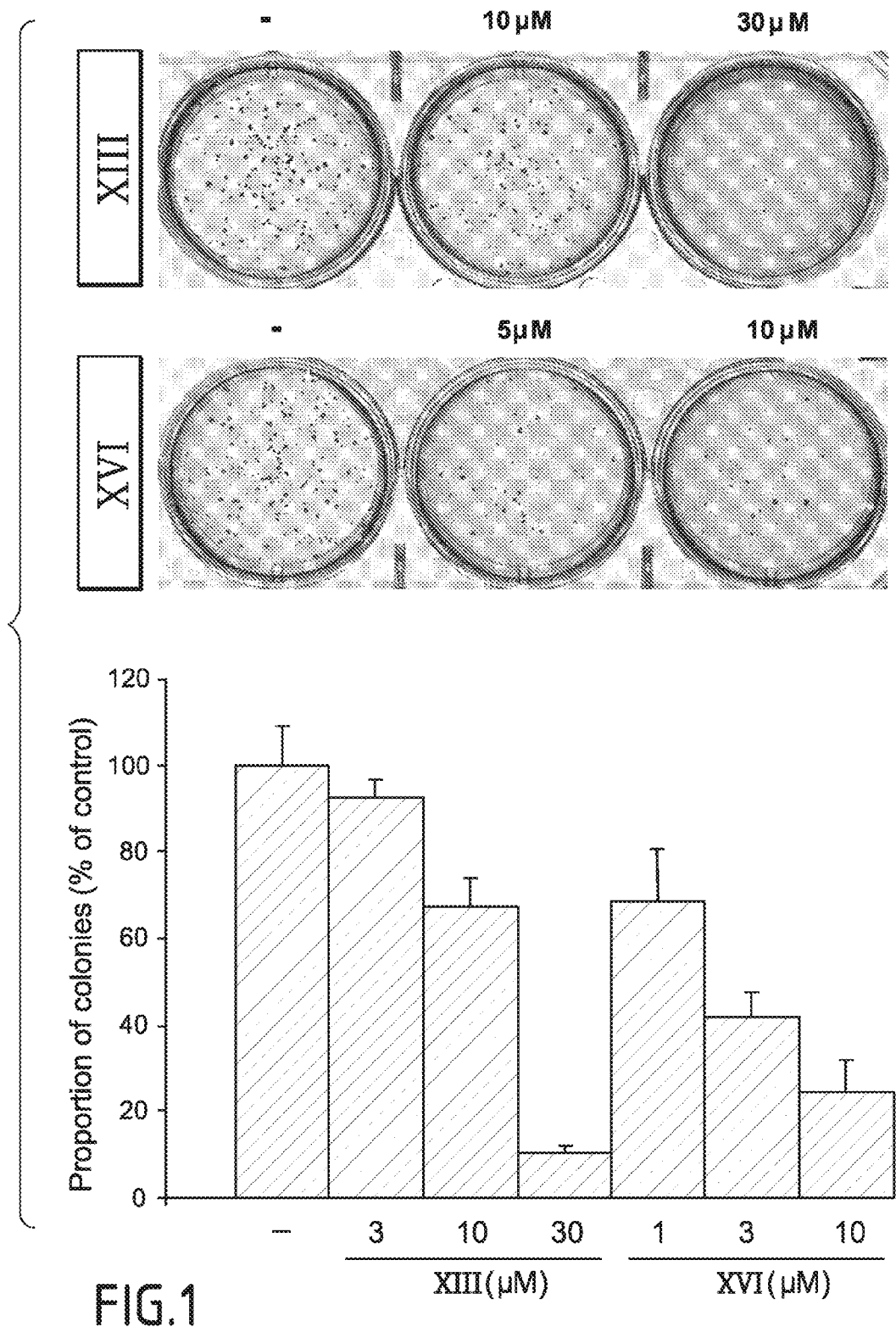
FIG. 1 represents the in vitro tumorigenesis inhibition by two compounds of the invention.

The following examples are given for illustration of the invention and are not intended to be limited thereof.
s: singlet
brs: broad singlet
d: doublet
brd: broad doublet
t: triplet
q: quadruplet
quint: quintuplet
dd: doubled doublet
dt: doubled triplet
dq: doubled quadruplet
sept: septuplet
m: massif Commercial compounds were purchased from Acros Organics, Sigma-Aldrich, Alfa Aesar, Chembridge and Maybridge.

CAS numbers of other building blocks are indicated in brackets.

Preparation 1

Preparation of (S) 2-[2-(3,5-dimethylphenyl)acetamido]-3-phenyl-propionic Acid

[General Formula (III) with W2=H; n=1; r=0; X=Ph; Y=CH$_2$—(3,5-Me)Ph]

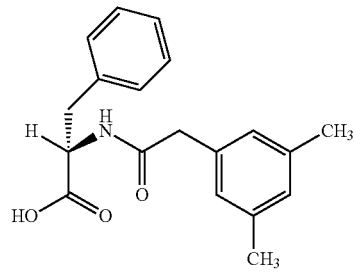

Step a.

SOCl$_2$ (4.35 ml, 59.39 mmol) was added dropwise in 5 min at 0° C. to a solution of L-Phenylalanine (3.0 g, 18.16 mmol) in dry methanol (40 ml) under nitrogen. The reaction mixture was stirred at 50° C. for 12 h.

The solvent was removed in vacuo. The crude solid was extracted with NaHCO$_3$ and Ethyl acetate and the organic phase was dried whit Na$_2$SO$_4$. The solvent was removed under reduced pressure. Methyl ester of L-Phenylalanine was obtained (90% c.y.) and used without any further purification for the following step Step b.

DMAP (4-dimethylaminopyridine) (17.0 mg, 1.40 mmol) and DCC (1,3-dicyclohexylcarbodiimide)(86.2 mg, 4.19 mmol) were added to a solution of 3,5-dimethylphenylacetic acid (500 mg, 2.79 mmol) in dry THF (50 ml) were added. The mixture was stirred at rt for 30 min and then methyl ester of L-Phenylalanine (461 mg, 2.79 mmol) was added. After 48 h at rt. the crude mixture was filtered over celite and the solvent was removed under reduced pressure. The product was purified by flash chromatography (hexane/ethyl acetate 2:1) to afford (S) methyl 2-[2-(3,5-dimethylphenyl)acetamido]-3-phenyl-propanoate as white solid (70% c.y.).

Step c.

A solution of NaOH 1N (7.8 ml, 7.83 mmol) was added to a methanolic solution (40 ml) of (S) methyl 2-[2-(3,5-dimethylphenyl)acetamido]-3-phenyl-propanoate (635 mg, 1.95 mmol) and the reaction mixture was stirred for 1 h at rt, then concentrated under reduced pressure and residue diluted with H$_2$O (40 ml) and HCl 1N to obtain a pH value equal to 2. The crude organic product was extracted with ethyl acetate (3×40 ml) and the organic phase was dried with anhydrous Na$_2$SO$_4$. The solvent was removed under reduced pressure to afford (S) 2-[2-(3,5-dimethylphenyl)acetamido]-3-phenyl-propionic acid as white solid with nearly quantitative yield.

Analytical Data:

$^1$H NMR (CDCl$_3$, 400 MHz): δ 7.24-7.19 (3H, m), 6.70-6.94 (3H, m), 6.78 (2H, s), 6.01 (1H, d, J=7.6 Hz), 4.87-4.87-4.83 (1H, m), 3.53 (1H, d, J=16.4 Hz), 3.48 (1H, d, J=16.4 Hz), 3.16 (1H, dd, J=14.0, 5.6 Hz), 3.06 (1H, dd, J=14.0, 6.0 Hz), 2.30 (6H, s); $^{13}$C NMR (CDCl$_3$, 400 MHz): δ 174.36, 172.18, 138.63, 135.44, 133.68, 129.67, 129.24, 128.54, 127.26, 127.08, 53.17, 43.20, 36.99, 21.23;

MS-ES m/z 311 (M+H)$^+$.

$[α]^{25}_D$+35.0 (CHCl$_3$).

Using analogous procedures the other N-acyl-amino acids of general formula (III) were so obtained.

Preparation 2

Preparation of 4-[(imidazo[2,1-b]benzothiazol-2-yl)aniline

[General Formula (II) with m=p=0, T=W1=H]

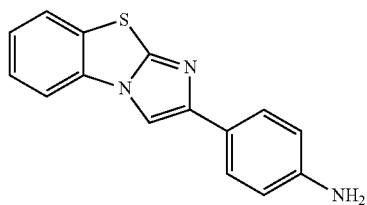

A mixture of 2-aminobenzothiazole (4.00 g, 26.6 mmol) and 2-bromo-4'-nitroacetophenone (7.32 g, 30.0 mmol) was refluxed in ethanol for 90 min and then the mixture was cooled to 0° C. The solid (about 2 g) was collected by filtration, washed with the minimum quantity of cold ethanol and then dissolved again in 150 ml of ethanol and added of iron powder (7.47 g, 133.75 mmol), water (30 ml) and $H_2SO_4$ 12N (750 μl). The mixture was stirred at 90° C. for 1 h, then filtered on celite and washed with hot ethanol. The solvent was removed under reduced pressure and the crude material was treated with aqueous $NaHCO_3$ (10%, 400 ml) and extracted with $CH_2Cl_2$ (3×150 ml). The organic phase was dried with anhydrous $Na_2SO_4$ and the solvent removed under reduced pressure to afford 4-[(imidazo[2,1-b]benzothiazol-2-yl) aniline.

Analytical Data:
$^1$H NMR (DMSO-d6, 300 MHz): δ 8.48 (1H, s), 8.05 (1H, d, J=8.0 Hz), 7.93 (1H, d, J=8.0 Hz), 7.61-7.51 (3H, m), 7.42 (1H, t, J=8.0 Hz), 6.64 (2H, d, J=9.0 Hz), 5.23 (2H, s); MS-ES m/z 265 (M+H)$^+$.

Using analogous procedures other compounds of general formula (II) may be obtained.

Preparation 3

Preparation of [4-(7-(2-morpholin-4-yl-ethoxy)imidazo[2,1-Mbenzothiazol-2-yl]aniline

[General Formula (II) with m=1, p=0; $R_1$=(2-morpholin-4-yl)-eth-7-oxy; T=W1=H]

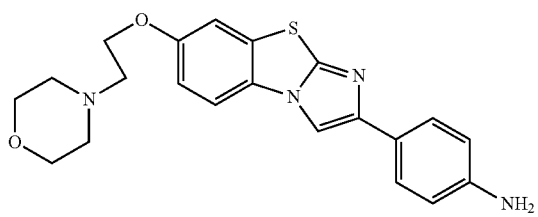

This product was prepared according to *J. Med. Chem.* 2009, 52, 7808-7816 with some modifications. A mixture of 2-amino-1,3-benzothiazol-6-ol (2.0 g, 12.18 mmol) and 2-bromo-4'-nitroacetophenone (2.97 g, 12.18 mmol) in IPA (40 ml) was heated to reflux for 24 h. The reaction mixture was then cooled to 0° C. and the resulting precipitate was filtrated and washed with IPA to afford 2-(4-nitrophenyl) imidazo[2,1-b][1,3]benzothiazol-7-ol (65% c.y.). To a DMF (52 ml) solution of 2-(4-nitrophenyl)imidazo[2,1-b][1,3]benzothiazol-7-ol was added potassium carbonate (2.94 g) and 4-(2-chloroethyl)morpholine hydrochloride (1.97 g). The reaction mixture was heated to 85° C. and stirred at the same temperature for 48 h. Then it was poured into water (100 ml), filtered and washed with water and ethyl ether to give 7-(2-morpholin-4-yl-ethoxy)-2-(4-nitrophenyl)imidazo[2,1-b][1,3]benzothiazole (86% c.y.). A mixture of 7-(2-morpholin-4-yl-ethoxy)-2-(4-nitrophenyl)imidazo[2,1-b][1,3] benzothiazole and ammonium chloride (0.77 g) in ethanol (50 ml) was heated to reflux, and then iron powder (3.0 g) was added. The mixture was refluxed for 5 h and then immediately filtered though Celite and washed with hot ethanol. The filtrate was concentrated, neutralized with saturated $NaHCO_3$ solution and extracted with DCM. The organic solution was dried with $Na_2CO_3$ and the solvent was removed under reduced pressure to afford the desired product [4-(7-(2-morpholin-4-yl-ethoxy)imidazo[2,1-b]benzothiazol-2-yl]aniline (32% c.y.).

Preparation 4

Preparation of [4-(6-(2-morpholin-4-yl-ethoxy)imidazo[2,1-b]benzothiazol-2-yl]aniline

[General Formula (II) with m=1, p=0; $R_1$=(2-morpholin-4-yl)-eth-6-oxy; T=W1=H]

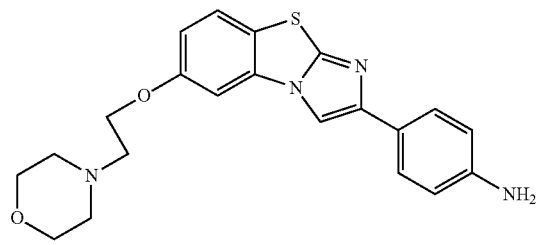

This product was prepared according to *J. Med. Chem.* 2009, 52, 7808-7816 but with the same modifications adopted in preparation 3 and using 2-amino-1,3-benzothiazol-5-ol instead of 2-amino-1,3-benzothiazol-6-ol. The desired product [4-(6-(2-morpholin-4-yl-ethoxy)imidazo[2,1-b]benzothiazol-2-yl]aniline was so obtained.

Preparation 5

Preparation of (S)-2-[2-(4-methylphenyl)acetamido]-3-phenyl-propionic Acid

[General Formula (III) with W2=H; n=1; r=0; X=Ph; Y=$CH_2$-(4-Me)Ph]

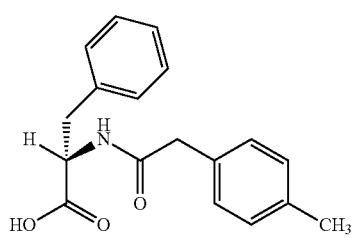

DMAP (194 mg, 1.58 mmol) and DIC (N,N-diisopropylcarbodiimide) (740 μl, 4.76 mmol) were added to a solution of L-phenylalanine methyl ester hydrochloride (684 mg, 3.17 mmol) and p-tolylacetic acid (500 mg, 3.33 mmol) in dry DCM (35 ml). After 24 h at room temperature the solvent was removed under reduced pressure and the crude residue was purified by flash chromatography (DCM containing 1% EtOH) to afford (S)-methyl 2-[2-(4-methylphenyl)acetamido]-3-phenyl-propanoate in quantitative yield. The product was diluted with methanol (78 ml) and then an aqueous solution of NaOH (1N, 14.2 ml, 14.2 mmol) was added. The reaction mixture was stirred for 1 h at room temperature and concentrated. Then water and HCl 1N was added until pH 2. The organic product was extracted with DCM (3×50 ml), dried with $Na_2CO_3$ and concentrated under reduced pressure to afford (S)-2-[2-(4-methylphenyl)acetamido]-3-phenyl-propionic acid as a white solid (94% c.y.)

Analytical Data:
$^1$H-NMR (CDCl$_3$, 400 MHz) δ in ppm: 2.36 (s, 3H, CH$_3$), 3.01 (dd, J=14.0, 6.8 Hz, 1H, CHCH$_2$Ph), 3.12 (dd, J=14.0, 5.4 Hz, 1H, CHCH$_2$Ph), 3.51 (s, 2H, COCH$_2$), 4.77 (dd, J=6.8, 5.4 Hz, 1H, CHCH$_2$Ph), 5.78 (d, J=7.6 Hz, 1H, NH), 6.92 (d, J=7.6 Hz, 2H—Ar), 7.01 (d, J=8.4 Hz, 2H—Ar), 7.12 (d, J=7.6 Hz, 2H—Ar), 7.17-7.23 (m, 3H—Ar); $^{13}$C-RMN (CDCl$_3$, 100.4 MHz) δ in ppm: 21.1 (CH$_3$), 36.8 (CH CH$_2$Ph), 42.9 (CH$_2$CO), 53.2 (CHCH$_2$Ph), 127.1, 128.6, 129.2, 129.3, 129.8 (CH—Ar), 130.7, 135.3, 137.2 (C—Ar), 172.1 (CO)

Preparation 6

Preparation of (S)-2-(2-(3,5-dimethylphenyl)acetamido)-3-(1H-indol-3-yl)propionic Acid

[General Formula (III) with W2=H; n=1; r=0; X=3-In; Y=CH$_2$-(3,5-Me)Ph]

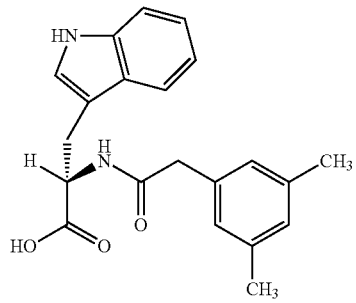

DMAP (122.2 mg, 0.5 mmol) and DIC (N,N-diisopropylcarbodiimide) (235 μl, 1.5 mmol) were added to a solution of tryptophan methyl ester (255 mg, 1.0 mmol) and 3,5-dimethylphenylacetic acid (164 mg, 1.0 mmol) in dry DCM (11 ml). After 17 h at room temperature the solvent was removed under reduced pressure and the crude product was purified by flash chromatography (DCM containing 1% EtOH) to afford (S)-methyl 2-(2-(3,5-dimethylphenyl)acetamido)-3-(1H-indol-3-yl)propanoate. An aqueous solution of LiOH (1N, 4.5 ml, 4.5 mmol) was added to a solution of (S)-methyl 2-(2-(3,5-dimethylphenyl)acetamido)-3-(1H-indol-3-yl)propanoate (365 mg, 1 mmol) in methanol (24.5 ml) and the reaction mixture was stirred at room temperature for 4.5 h. Then water was added and methanol was removed under reduced pressure. The aqueous residue was washed with DCM (5×20 ml), treated with HCl 2N to obtain a pH 4 and extracted with DCM (3×25 ml). The organic phases were dried with anhydrous Na$_2$SO$_4$ and the solvent was removed under reduced pressure to afford (S)-2-(2-(3,5-dimethylphenyl)acetamido)-3-(1H-indol-3-yl)propionic acid (93% c.y.).

Analytical Data:
$^1$H-NMR (CDCl$_3$, 400 MHz) δ in ppm: 2.18 (s, 6H, 2CH$_3$), 3.24 (dd, J=14.8, 5.6 Hz, 1H, CHCH$_2$Ind), 3.32 (dd, J=14.8, 5.2 Hz, 1H, CHCH$_2$Ind), 3.38 (s, 2H, COCH$_2$), 4.81-4.86 (m, 1H, CHCH$_2$Ind), 6.12 (d, J=6.4 Hz, 1H, NH), 6.64 (s, 2H—Ar), 6.8 (d, J=7.6 Hz, 2H, Ar), 7.04 (dd, J=8.0, 8.0 Hz, 1H—Ar), 7.14 (dd, J=7.6, 7.6 Hz, 1H—Ar), 7.27 (d, J=8.4 Hz, 1H—Ar), 7.45 (d, J=8.0 Hz, 1H—Ar)

Preparation 7

Preparation of (S)-2-(2-(3,5-bis(trifluoromethyl)phenyl)acetamido)-3-(1H-indol-3-yl) propionic Acid

[General Formula (III) with W2=H; n=1; r=0; X=3-In; Y=CH$_2$-(3,5-F$_3$C)Ph]

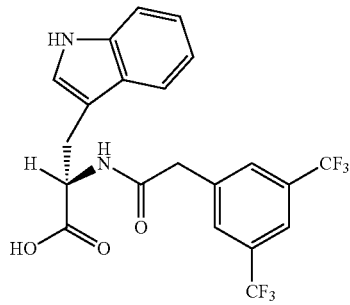

Working as in preparation 6, but using 3,5-bis(trifluoromethyl)phenylacetic acid instead of 3,5-dimethylphenylacetic acid, (S)-2-(2-(3,5-bis(trifluoromethyl)phenyl)acetamido)-3-(1H-indol-3-yl)propionic acid was obtained (93% c.y.)

Analytical Data:
$^1$H-NMR (CDCl$_3$, 300 MHz) δ in ppm: 3.36 (dd, J=10.5, 5.4 Hz, 2H, CHCH$_2$Ind), 3.53 (s, 2H, COCH$_2$), 4.90-4.96 (m, 1H, CHCH$_2$Ind), 6.11 (d, J=7.5 Hz, 1H, NH), 6.93 (d, J=2.4 Hz, 1H—Ar), 7.06 (dd, J=7.8, 7.8 Hz, 1H—Ar), 7.18 (dd, J=7.8, 7.8 Hz, 1H—Ar), 7.33 (d, J=7.8 Hz, 1H—Ar), 7.47 (d, J=7.8 Hz, 1H—Ar), 7.62 (s, 2H—Ar), 7.75 (s, 1H—Ar).

Example 1

(S)-2-(3,5-dimethylphenylacetamido)-3-phenyl-N-[4-(imidazo[2,1-b]benzothiazol-2-yl)phenyl]propanamide (XIII)

[General Formula (I) with m=p=r=0, T=W1=W2=H; n=1; X=Ph; Y=CH$_2$-(3,5-Me)Ph]

(XIII)

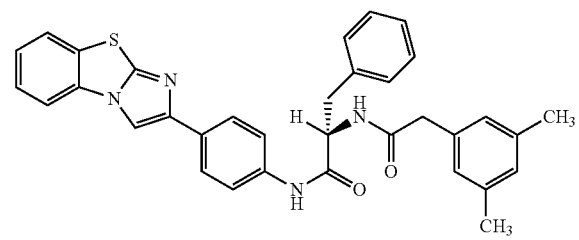

BOP-Cl (114.5 mg, 0.450 mmol), HOBT (33.4 mg, 0.247 mmol) and DIPEA (157 µl, 0.899 mmol) were added to a solution of (S) 2-[2-(3,5-dimethylphenyl)acetamido]-3-phenyl-propanoic acid (70.0 mg, 0.225 mmol) in dry $CH_2Cl_2$ (10 ml). After 10 min 4-[(imidazo[2,1-b]benzothiazol-2-yl) aniline (65.1 mg, 0.247 mmol) was added to the solution and the reaction mixture was reflux under nitrogen for 6 h. The solvent was removed under reduced pressure and the crude mixture was purified by flash chromatography (MeOH 2.5%-$CH_2Cl_2$ 97.5%) to afford the desired product (S)-2-(3,5-dimethylphenylacetamido)-3-phenyl-N-[4-(imidazo[2,1-b]benzothiazol-2-yl)phenyl]propanamide as a yellow solid (42% c.y.).

Analytical Data:
$^1$H NMR (CDCl$_3$, 400 MHz): δ 8.60 (1H, s), 7.92 (1H, s), 7.79 (2H, d, J=8.4 Hz), 7.70 (1H, d, J=7.8 Hz), 7.61 (1H, d, J=7.8 Hz), 7.48-7.44 (3H, m), 7.37 (1H, t, J=7.8 Hz), 7.29-7.21 (3H, m), 7.12-7.10 (2H, m), 6.95 (1H, s), 6.78 (2H, s), 6.29 (1H, d, J=7.6 Hz), 4.92-4.86 (1H, m), 3.51-3.47 (2H, m), 3.14 (1H, dd, J=14.0, 6.4 Hz), 3.05 (1H, dd, J=14.0, 7.8 Hz), 2.30 (6H, s); $^{13}$C NMR (CDCl$_3$, 100.6 MHz): δ 172.60, 170.02, 148.34, 146.43, 139.19, 138.16, 137.08, 134.73, 132.56, 131.01, 130.79, 129.91 (2C), 129.76, 129.22 (2C), 127.78, 127.56, 127.16, 126.44 (2C), 125.91, 124.80, 121.00 (2C), 113.68, 107.62, 55.99, 44.11, 38.48, 21.84 (2C)

m.p. 224-226° C.
$[α]^{25}_D$+5.80 (CHCl$_3$).
(elemental analysis) C, 73.21%; H, 5.38%; N, 10.00%; S, 5.68%.

Example 2

(R)-2-(3,5-dimethylphenylacetamido)-3-phenyl-N-[4-(imidazo[2,1-b]benzothiazol-2-yl)phenyl]propanamide (XIV)

[General Formula (I) with m=p=r=0, T=W1=W2=H; n=1; X=Ph; Y=CH$_2$-(3,5-Me)Ph]

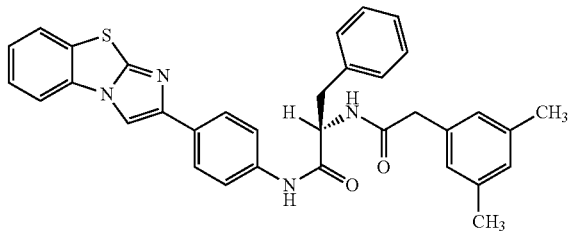

(XIV)

Working as in the example 1, but using (R) 2-[2-(3,5-dimethylphenyl)acetamido]-3-phenyl-propanoic acid, the desired product (R)-2-(3,5-dimethylphenylacetamido)-3-phenyl-N-[4-(imidazo[2,1-b]benzothiazol-2-yl)phenyl]propanamide was obtained.

Analytical Data:
$^1$H NMR (CDCl$_3$, 400 MHz): δ 8.60 (1H, s), 7.92 (1H, s), 7.79 (2H, d, J=8.4 Hz), 7.70 (1H, d, J=7.8 Hz), 7.61 (1H, d, J=7.8 Hz), 7.48-7.44 (3H, m), 7.37 (1H, t, J=7.8 Hz), 7.29-7.21 (3H, m), 7.12-7.10 (2H, m), 6.95 (1H, s), 6.78 (2H, s), 6.29 (1H, d, J=7.6 Hz), 4.92-4.86 (1H, m), 3.51-3.47 (2H, m), 3.14 (1H, dd, J=14.0, 6.4 Hz), 3.05 (1H, dd, J=14.0, 7.8 Hz), 2.30 (6H, s); $^{13}$C NMR (CDCl$_3$, 100.6 MHz): δ 172.60, 170.02, 148.34, 146.43, 139.19, 138.16, 137.08, 134.73, 132.56, 131.01, 130.79, 129.91 (2C), 129.76, 129.22 (2C), 127.78, 127.56, 127.16, 126.44 (2C), 125.91, 124.80, 121.00 (2C), 113.68, 107.62, 55.99, 44.11, 38.48, 21.84 (2C)

m.p. 224-226° C.
$[α]^{25}_D$-4.28 (CHCl$_3$).
(elemental analysis) C, 73.12%; H, 5.45%; N, 10.00%; S, 5.70%.

Example 3

(S)-2-(3,5-dimethylphenylacetamido)-3-(4-hydroxyphenyl)-N-[4-(imidazo[2,1-b]benzothiazol-2-yl) phenyl]propanamide (XV)

[General Formula (I) with m=p=r=0, T=W1=W2=H; n=1; X=(4-OH)Ph; Y=CH$_2$-(3,5-Me)Ph]

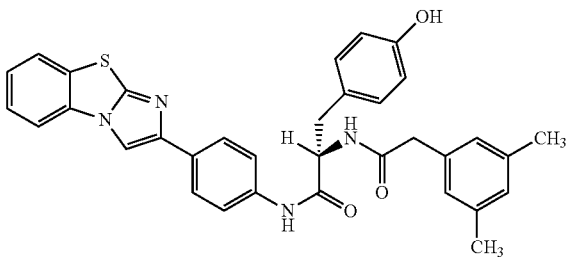

(XV)

Working as in the example 1, but using (S) 2-[2-(3,5-dimethylphenyl) acetamido]-3-(4-hydroxy)phenyl-propanoic acid, the desired product (S)-2-(3,5-dimethylphenylacetamido)-3-(4-hydroxyphenyl)-N-[4-(imidazo[2,1-b] benzothiazol-2-yl)phenyl]propanamide was recovered.

Analytical Data:
$^1$H NMR (DMSO-d6, 300 MHz): δ 10.25 (1H, s), 8.73 (1H, s), 8.39 (1H, d, J=7.8 Hz), 8.08 (1H, d, J=8.1 Hz), 7.98 (1H, d, J=8.1 Hz), 7.81 (2H, d, J=8.6 Hz), 7.67 (2H, d, J=8.6 Hz), 7.58 (1H, t, J=8.1 Hz), 7.43 (1H, t, J=8.1 Hz), 7.11 (2H, d, J=7.5 Hz), 6.84 (1H, s), 6.78 (2H, s), 6.67 (2H, d, J=7.5 Hz), 5.89 (1H, s), 4.65-4.54 (1H, m), 3.48-3.30 (2H, m), 2.98 (1H, dd, J=14.2, 4.5 Hz), 2.81 (1H, dd, J=14.2, 9.3 Hz).

Example 4

(S)-2-(3,5-bis(trifluoromethyl)phenylacetamido)-3-phenyl-N-[4-(imidazo[2,1-b]benzothiazol-2-yl)phenyl]propanamide (XVI)

[General Formula (I) with m=p=r=0, T=W1=W2=H; n=1; X=Ph; Y=CH$_2$-(3,5-F$_3$C)Ph]

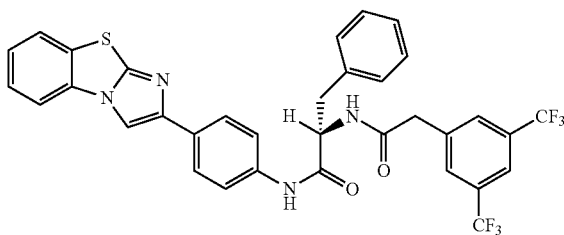

(XVI)

Working as in the example 1, but using (S) 2-[2-(3,5-bis (trifluoro-methyl)phenyl)acetamido]-3-phenyl-propanoic acid and reagents as HATU and DIPEA in THF at room temperature for the condensation, the desired product (S)-2-(3,5-bis(trifluoromethyl)phenylacetamido)-3-phenyl-N-[4-(imidazo[2,1-b]benzothiazol-2-yl)phenyl]propanamide was recovered in nearly quantitative yield.

Analytical Data:
$^1$H NMR (DMSO-d6, 400 MHz): δ 10.25 (1H, s), 8.71-8.69 (2H, m), 8.04 (1H, d, J=8.0 Hz), 7.98 (1H, d, J=8.0 Hz), 7.96 (1H, s), 7.90 (2H, s), 7.82 (2H, d, J=8.6 Hz), 7.66 (2H, d, J=8.6 Hz), 7.58 (1H, t, J=8.0 Hz), 7.44 (1H, t, J=8.0 Hz), 7.29-7.13 (5H, m), 4.75-4.70 (1H, m), 3.74 (1H, d, J=15.1 Hz), 3.70 (1H, d, J=15.1 Hz), 3.10 (1H, dd, J=13.8, 4.8 Hz), 2.89 (1H, dd, J=13.8, 9.7 Hz). $^{13}$C NMR (DMSO-d6, 100.6 MHz): δ 172.13, 169.45, 146.82, 145.91, 141.12, 139.44, 138.87, 133.21, 131.98 (2C, q, J=33.2 Hz) 131.80, 131.01 (2C), 130.51, 130.23 (2C), 129.03 (2C), 127.79, 127.41, 126.23 (2C), 126.18, 126.10, 123.42 (2C, q, J=271.0 Hz), 121.79, 120.84 (2C), 114.37, 109.56, 56.04, 42.60, 38.65.

m.p. 243-245° C.

$[α]^{25}_D$+1.54 (DMSO).

(elemental analysis) C, 61.31; H, 3.60; F, 17.10; N, 8.38; S, 4.81.

Example 5

(R)-2-(3,5-bis(trifluoromethyl)phenylacetamido)-3-phenyl-N-[4-(imidazo[2,1-b]benzothiazol-2-yl)phenyl]propanamide (XVII)

[General Formula (I) with m=p=r=0, T=W1=W2=H; n=1; X=Ph; Y=CH$_2$-(3,5-F$_3$C)Ph]

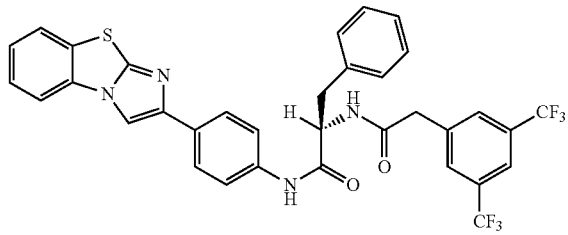

(XVII)

Working as in the example 4, but using (R) 2-[2-(3,5-bis(trifluoro-methyl)phenyl)acetamido]-3-phenyl-propanoic acid and reagents as HATU and DIPEA in THF at room temperature for the condensation, the desired product (R)-2-(3,5-bis(trifluoromethyl)phenylacetamido)-3-phenyl-N-[4-(imidazo[2,1-b]benzothiazol-2-yl)phenyl]propanamide was recovered in nearly quantitative yield.

Analytical Data:
$^1$H NMR (DMSO-d6, 400 MHz): δ 10.25 (1H, s), 8.71-8.69 (2H, m), 8.04 (1H, d, J=8.0 Hz), 7.98 (1H, d, J=8.0 Hz), 7.96 (1H, s), 7.90 (2H, s), 7.82 (2H, d, J=8.6 Hz), 7.66 (2H, d, J=8.6 Hz), 7.58 (1H, t, J=8.0 Hz), 7.44 (1H, t, J=8.0 Hz), 7.29-7.13 (5H, m), 4.75-4.70 (1H, m), 3.74 (1H, d, J=15.1 Hz), 3.70 (1H, d, J=15.1 Hz), 3.10 (1H, dd, J=13.8, 4.8 Hz), 2.89 (1H, dd, J=13.8, 9.7 Hz). $^{13}$C NMR (DMSO-d6, 100.6 MHz): δ 172.13, 169.45, 146.82, 145.91, 141.12, 139.44, 138.87, 133.21, 131.98 (2C, q, J=33.2 Hz) 131.80, 131.01 (2C), 130.51, 130.23 (2C), 129.03 (2C), 127.79, 127.41, 126.23 (2C), 126.18, 126.10, 123.42 (2C, q, J=271.0 Hz), 121.79, 120.84 (2C), 114.37, 109.56, 56.04, 42.60, 38.65.

m.p. 244-245° C.

$[α]^{20}_D$−1.47 (DMSO).

Example 6

(S)-2-(3,5-difluoromethylphenylacetamido)-3-phenyl-N-[4-(imidazo[2,1-b]benzothiazol-2-yl)phenyl]propanamide (XVIII)

[General Formula (I) with m=p=r=0, T=W1=W2=H; n=1; X=Ph; Y=CH$_2$-(3,5-F)Ph]

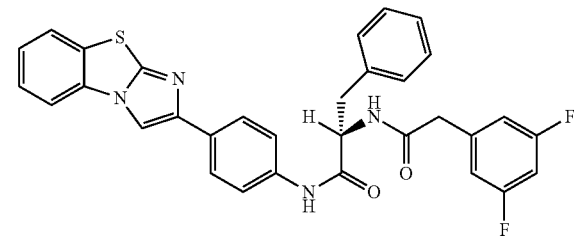

(XVIII)

Working as in the example 4, but using (S) 2-[2-(3,5-difluorophenyl)acetamido]-3-phenyl-propanoic acid, the desired product (S)-2-(3,5-difluorophenylacetamido)-3-phenyl-N-[4-(imidazo[2,1-b]benzothiazol-2-yl)phenyl]propanamide was obtained.

Analytical Data:
$^1$H NMR (DMSO-d6, 300 MHz): δ 10.27 (1H, s), 8.72 (1H, s), 8.61 (1H, d, J=8.2 Hz), 8.05 (1H, d, J=7.9 Hz), 7.99 (1H, d, J=7.9 Hz), 7.84 (2H, d, J=8.5 Hz), 7.67 (2H, d, J=8.5 Hz), 7.58 (1H, t, J=7.9 Hz), 7.44 (1H, t, J=7.9 Hz), 7.32-7.20 (5H, m), 7.09-7.05 (1H, m), 7.86 (2H, d, J=7.0 Hz), 4.75-4.71 (1H, m), 3.54 (1H, d, J=14.1 Hz), 3.48 (1H, d, J=14.1 Hz), 3.12 (1H, dd, J=13.6, 4.9 Hz) 2.90 (1H, dd, J=13.6, 9.8 Hz).

m.p. 242-243° C.

$[α]^{20}_D$−4.34 (MeOH/CHCl$_3$ 1/1)

Example 7

2-(3,5-dimethylphenylacetamido)-N-[4-(imidazo[2,1-b]benzothiazol-2-yl)phenyl]acetamide (XIX)

[General Formula (I) with m=p=r=0, T=W1=W2=H; n=0; X=H; Y=CH$_2$-(3,5-Me)Ph]

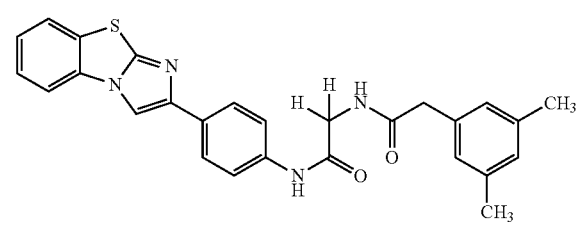

(XIX)

Working as in the example 4, but using 2-(3,5-dimethylphenyl)acetamido]-acetic acid, the desired product 2-(3,5-dimethylphenylacetamido)-N-[4-(imidazo[2,1-b]benzothiazol-2-yl)phenyl]acetamide was recovered in nearly quantitative yield.

Analytical Data:
$^1$H NMR (DMSO-d6, 300 MHz): δ 10.04 (1H, s), 8.71 (1H, s), 8.37-8.33 (1H, m), 8.05 (1H, d, J=7.9 Hz), 7.98 (1H, d, J=7.9 Hz), 7.82 (2H, d, J=8.6 Hz), 7.66 (2H, d, J=8.6 Hz), 7.59 (1H, t, J=7.9 Hz), 7.44 (1H, t, J=7.9 Hz), 6.92 (2H, s), 6.87 (1H, s), 3.92 (2H, d, J=5.6 Hz), 3.34 (2H, s), 2.26 (6H, s). m.p. 250-252° C.

Example 8

(S)-2-(3,5-bis(trifluoromethyl)phenylacetamido)-3-phenyl-N-[4-(7-bromo)imidazo[2,1-b]benzothiazol-2-yl)phenyl]propanamide (XX)

[General Formula (I) with m=1; p=r=0; $R_1$=7-Br; T=W1=W2=H; n=1; X=Ph; Y=$CH_2$-(3,5-$F_3$C)Ph]

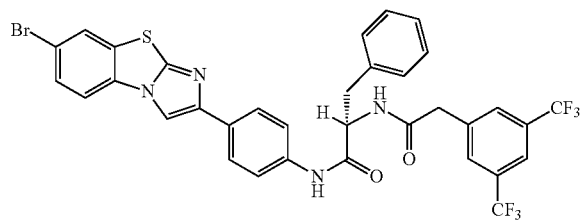
(XX)

Working as in the example 4, but using 4-[(7-bromo)imidazo[2,1-b]benzothiazol-2-yl)aniline, instead of 4-[imidazo[2,1-b]benzothiazol-2-yl)]aniline, and reagents as HATU and DIPEA in THF at room temperature for the condensation, the desired product (S)-2-(3,5-bis(trifluoromethyl)phenylacetamido)-3-phenyl-N-[4-(7-bromo)imidazo[2,1b]benzothiazol-2-yl)phenyl]propanamide was recovered. The crude product was purified by flash chromatography (Hex:AcOEt 1:1) and then crystallized by $CH_3CN$. (48% c.y.)

Analytical Data:
$^1$H NMR (DMSO-d6, 400 MHz): δ 10.26 (1H, s), 8.71 (1H, d, J=8.7 Hz), 8.70 (1H, s), 8.34 (1H, d, J=1.8 Hz), 7.95 (1H, s), 7.93 (1H, d, J=8.5 Hz), 7.89 (2H, s), 7.81 (2H, d, J=8.7 Hz), 7.75 (1H, dd, J=8.5, 1.8 Hz), 7.66 (2H, d, J=8.7 Hz), 7.27-7.13 (5H, m), 4.75-4.69 (1H, m), 3.75 (1H, d, J=16.4 Hz), 3.70 (1H, d, J=16.4 Hz), 3.10 (1H, dd, J=13.8, 4.8 Hz), 2.89 (1H, dd, J=13.8, 9.8 Hz); $^{13}$C NMR (DMSO-$d_6$, 100.6 MHz): δ 170.48, 169.49, 147.42, 146.85, 140.10, 138.44, 137.86, 131.82, 131.59, 130.58 (2C, q, J=37 Hz), 130.37 (2C), 129.99, 129.59, 129.50, 128.40 (2C), 127.86, 126.80 (2C), 125.60 (2C), 123.85 (2C, q, J=272 Hz), 120.68, 120.11, 117.12, 115.29, 109.14, 55.42, 41.48, 38.30.
$[α]^{20}_D$=+2.95 (DMSO)

Example 9

(S)-2-(4-methylphenylacetamido)-3-phenyl-N-[4-(imidazo[2,1-b]benzothiazol-2-yl)phenyl]propanamide (XXI)

[General Formula (I) with m=p=r=0, T=W1=W2=H; n=1; X=Ph; Y=$CH_2$-(4-Me)Ph]

(XXI)
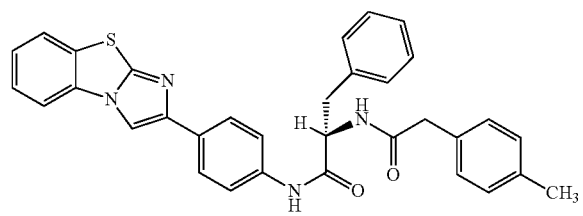

Working as in the example 4, but using (S) 2-[2-(4-methylphenyl)acetamido]-3-phenyl-propionic acid, and reagents as HATU and DIPEA in THF at room temperature for the condensation, the desired product (S)-2-(4-methylphenylacetamido)-3-phenyl-N-[4-(imidazo[2,1-b]benzothiazol-2-yl)phenyl]propanamide was obtained. The crude product was purified by flash chromatography (DCM containing 5% MeOH) (57% c.y.)

Analytical Data:
$^1$H-NMR (CDCl$_3$ with drops of CD$_3$OD, 500 MHz) δ in ppm: 2.27 (s, 3H, CH$_3$), 2.92 (dd, J=14.0, 7.5 Hz, 1H, CHCH$_2$Ph), 3.05 (dd, J=14.0, 7.5 Hz, 1H, CHCH$_2$Ph), 3.43 (s, 2H, CH$_2$CO), 4.70 (dd, J=7.5, 7.5 Hz, 1H, CHCH$_2$Ph), 6.98 (d, J=7.5 Hz, 2H—Ar), 7.04-7.06 (m, 4H—Ar), 7.16-7.17 (m, 3H—Ar), 7.29 (dd, J=7.5, 7.5 Hz, 1H—Ar), 7.39-7.43 (m, 3H—Ar), 7.57 (d, J=8.0 Hz, 1H—Ar), 7.65 (d, J=8.0 Hz, 1H—Ar), 7.68 (d, J=8.0 Hz, 2H—Ar), 7.89 (s, 1H, NCHCN); $^{13}$C-RMN (CDCl$_3$ with drops of CD$_3$OD, 125.7 MHz) δ in ppm: 20.8 (CH$_3$), 38.1 (CHCH$_2$Ph), 42.6 (CH$_2$CO), 54.7 (CHCH$_2$Ph), 106.7, 112.6, 120.2, 124.2, 124.9, 125.5, 126.3, 126.7, 128.3, 128.9, 129.1, 129.4 (CH—Ar), 129.5, 129.8, 131.0, 131.9, 135.9, 136.7, 136.9, 146.7, 148.0 (C—Ar), 169.4, 172.0 (CO).

Example 10

(S)-2-(3,5-dimethyl)phenylacetamido)-3-(4-methylphenyl)-N-[4-(imidazo[2,1-b]benzothiazol-2-yl)phenyl]propanamide (XXII)

[General Formula (I) with m=p=r=0, T=W1=W2=H; n=1; X=(4-Me)Ph; Y=$CH_2$-(3,5-Me)Ph]

(XXII)
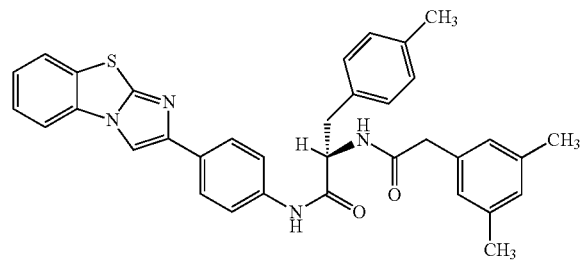

HATU (258 mg, 0.68 mmol) and DIPEA (197 μl, 1.13 mmol) were added to a solution of 4-[(imidazo[2,1-b]benzothiazol-2-yl)]aniline (150 mg, 0.56 mmol) and N-Boc-4-methylphenylalanine (158 mg, 0.56 mmol) in dry THF (11 ml). After 48 h at room temperature the solvent was removed under reduced pressure and the crude mixture was purified by flash chromatography (DCM containing 1% MeOH) to afford the desired N-Boc derivative that was dissolved in dry DCM (5 ml). TFA (5 ml) was then added and the reaction mixture was stirred at room temperature for 4 hours. Then the solvent was removed under reduced pressure and the crude mixture was purified by flash chromatography (DCM containing 10% EtOH) to afford 2-amino-3-(4-methylphenyl)-N-[4-(imidazo[2,1-b]benzothiazol-2-yl)phenyl]-propanamide in nearly quantitative yield. A suspension of 2-amino-3-(4-methylphenyl)-N-[4-(imidazo[2,1-b]benzothiazol-2-yl]phenyl]propanamide (150 mg, 0.35 mmol) in dry DCM (4 ml) was then mixed to 3,5-dimethylphenylacetic acid (60.6 mg, 0.37 mmol) and DMAP (21.5 mg, 0.17 mmol). Once the solution was obtained, DIC (83 l, 0.53 mmol) was added. After 4.5 h at room temperature the solvent was removed under reduced pressure and the crude mixture was purified by flash chromatography (DCM containing 2% EtOH) to afford (S)-2-(3,5-dimethylphenylacetamido)-3-(4-methylphenyl)-N-[4-(imidazo[2,1-b]benzothiazol-2-yl)phenyl]propanamide that was further on purified by crystallization in CHCl$_3$ (32% c.y.)

Analytical Data:

$^1$H-NMR (CDCl$_3$, 400 MHz) δ in ppm: 2.27 (s, 6H, 2CH$_3$), 2.32 (s, 3H, CH$_3$), 3.02-3.08 (m, 2H, CHCH$_2$Ph), 3.49 (s, 2H, CH$_2$CO), 4.77 (dd, J=14.4, 7.6 Hz, 1H, CHCH$_2$Ph), 6.14 (d, J=7.5 Hz, NH), 6.75 (s, 2H—Ar), 6.92 (s, 1H—Ar), 6.98 (d, J=7.6 Hz, 2H—Ar), 7.05 (d, J=7.6 Hz, 2H—Ar), 7.32 (dd, K=7.6, 7.6 Hz, 1H—Ar), 7.41-7.45 (m, 3H—Ar), 7.56 (d, J=7.6 Hz, 1H—Ar), 7.63 (d, J=7.6 Hz, 2H—Ar), 7.74-7.77 (m, 2H—Ar), 7.87 (s, 1H—Ar), 8.36 (s, 1H, NH); $^{13}$C-RMN (CDCl$_3$, 100.4 MHz) δ in ppm: 21.1 (CH$_3$), 21.2 (CH$_3$), 29.7 (CH$_3$), 36.7 (CHCH$_2$Ph), 43.4 (CH$_2$CO), 55.3 (CHCH$_2$Ph), 106.5, 112.6, 120.2, 124.3, 124.8, 125.7, 126.2, 127.1, 129.1, 129.2, 129.4 (CH—Ar), 130.0, 130.2, 132.1, 133.1, 133.8, 136.5, 136.9, 138.7, 147.2, 148.0 (C—Ar), 169.0, 172.1 (CO).

Example 11

(S)-2-(3,5-bis(trifluoromethyl)phenylacetamido)-3-(4-methylphenyl)-N-[4-(imidazo[2,1-b]benzothiazol-2-yl)phenyl]propanamide (XXIII)

[General Formula (I) with m=p=r=0, T=W1=W2=H; n=1; X=(4-Me)Ph; Y=CH$_2$-(3,5-F$_3$C)Ph]

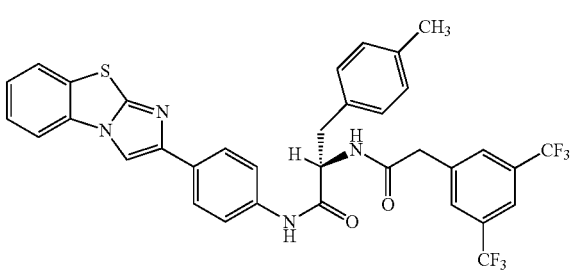

(XXIII)

Working as in the example 10, but using 3,5-bis(trifluoromethyl)phenylacetic acid instead of 3,5-dimethylphenylacetic acid, the desired product (S)-2-(3,5-bis(trifluoromethyl)phenylacetamido)-3-(4-methylphenyl)-N-[4-(imidazo[2,1-b]benzothiazol-2-yl)phenyl]propanamide was obtained (44% c.y.)

Analytical Data:

$^1$H-NMR (CDCl$_3$, 400 MHz) δ in ppm: 2.23 (s, 3H, CH$_3$), 2.94 (dd, J=14.0, 7.2 Hz, 1H, CHCH$_2$Ph), 3.06 (dd, J=14.0, 7.5 Hz, 1H, CHCH$_2$Ph), 3.58 (s, 2H, CH$_2$CO), 4.68 (dd, J=7.2, 7.2 Hz, 1H, CHCH$_2$Ph), 6.99 (2, 4H—Ar), 7.33 (dd, J=8.2, 8.2 Hz, 1H—Ar), 7.42 (d, J=8.2 Hz, 1H—Ar), 7.46 (s, 1H—Ar), 7.48 (s, 1H—Ar), 7.61 (d, J=7.2 Hz, 1H—Ar), 7.68-7.70 (m, 3H—Ar), 7.73-7.75 (3H—Ar), 7.92 (s, 1H—Ar).

Example 12

(S)-2-(3,5-dimethylphenylacetamido)-3-(1H-indol-3-yl)-N-[4-(imidazo[2,1-b]benzothiazol-2-yl)phenyl]propanamide (XXIV)

[General Formula (I) with m=p=r=0, T=W1=W2=H; n=1; X=3-In; Y=CH$_2$-(3,5-Me)Ph]

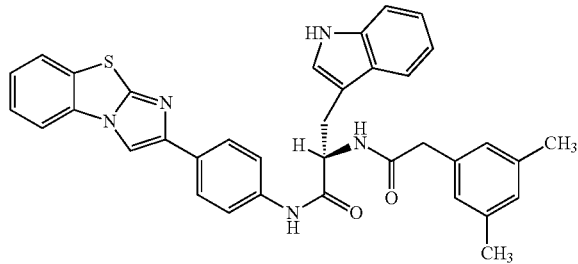

(XXIV)

Working as in the example 1, but using (S)-2-(2-(3,5-dimethylphenyl)acetamido)-3-(1H-indol-3-yl)propionic acid and reagents as HATU and DIPHEA in THF at room temperature, the desired compound (S)-2-(2-(3,5-dimethylphenyl)acetamido)-3-(1H-indol-3-yl)-N-[4-(imidazo[2,1-b]benzothiazol-2-yl)phenyl]propanamide was obtained (10% c.y.)

Analytical Data:

$^1$H-NMR (CDCl$_3$ with drops of CD$_3$OD, 400 MHz) δ in ppm: 2.25 (s, 6H, 2CH$_3$), 3.22-3.33 (m, 2H, CHCH$_2$Ind), 3.47 (s, 2H, CH$_2$CO), 4.84 (dd, J=14.0, 6.8 Hz, 1H, CHCH$_2$Ind), 6.77 (s, 2H—Ar), 6.88 (s, 1H—Ar), 6.96 (s, 1H—Ar), 7.05 (dd, J=8.0, 8.0 Hz, 1H-Ar), 7.15 (dd, J=8.0, 8.0 Hz, 1H—Ar), 7.20 (d, J=7.6 Hz, NH), 7.36-7.52 (m, 5H—Ar), 7.60 (d, J=7.6 Hz, 1H—Ar), 7.72 (dd, J=76.8, 7.8 Hz, 4H—Ar), 8.05 (s, 1H—Ar); $^{13}$C-RMN (CDCl$_3$ with drops of CD3OD, 100.4 MHz) δ in ppm: 20.5 (CH$_3$), 27.7 (CHCH$_2$Ind), 42.6 (CH$_2$CO), 54.3 (CHCH$_2$Ind), 106.8, 111.0, 112.6, 118.0, 118.7, 120.1, 121.23, 123.0, 124.0, 124.8, 125.2, 126.1, 126.6, 128.4 (CH—Ar), 108.8, 127.0, 129.2, 129.5, 131.7, 133.9, 136.0, 136.8, 137.9, 146.5, 147.8 (C—Ar), 169.9, 172.0 (CO).

Example 13

(S)-2-(3,5-bis(trifluoromethylphenylacetamido)-3-(1H-indol-3-yl)-N-[4-(imidazo[2,1-b]benzothiazol-2-yl)phenyl]propanamide (XXV)

[General Formula (I) with m=p=r=0, T=W1=W2=H; n=1; X=3-In; Y=CH$_2$-(3,5-F3C)Ph]

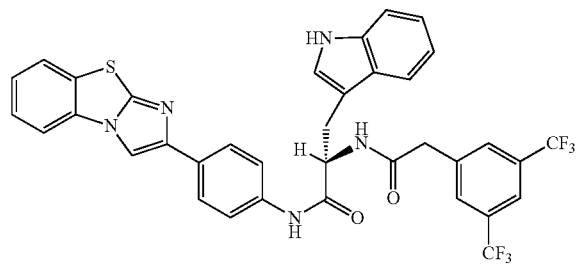

(XXV)

Working as in example 12, but using (S)-2-(2-(3,5-bis(trifluoromethyl)-phenyl)acetamido)-3-(1H-indol-3-yl)propionic acid, the desired product (S)-2-[2-(3,5-bis(trifluoromethyl)phenyl)acetamido]-3-(1H-indol-3-yl)-N-[4-(imidazo[2,1-b]benzothiazol-2-yl)phenyl]propanamide was obtained (51% c.y.)

Analytical Data:
$^1$H-NMR (CDCl$_3$ with drops of CD$_3$OD, 400 MHz) δ in ppm: 3.24-3.29 (m, 2H, CHCH$_2$Ind), 3.68 (d, J=4.8 Hz, 2H, CH$_2$CO), 4.85 (dd, J=7.0, 7.0 Hz, 1H, CHCH$_2$Ind), 7.02-7.06 (m, 2H—Ar), 7.14 (dd, J=7.4, 7.4 Hz, 1H—Ar), 7.37 (d, J=8.0 Hz, 1H—Ar), 7.43-7.49 (m, 4H—Ar), 7.54-7.57 (m, 1H—Ar), 7.61 (d, J=8.0 Hz, 1H—Ar), 7.70-7.76 (m, 5H—Ar), 7.81 (d, J=8.4 Hz, 2H—Ar), 8.19 (s, NH); $^{13}$C-RMN (CDCl$_3$ with drops of CD3OD, 100.4 MHz) δ in ppm: 27.9 (CHCH$_2$Ind), 41.3 (CH$_2$CO), 54.7 (CHCH$_2$Ind), 107.6, 111.1, 113.3, 117.8, 118.6, 119.9, 120.3, 121.2, 123.0, 124.3, 125.4, 125.9, 126.9, 129.3 (CH—Ar), 108.9, 131.0, 131.3, 136.0, 137.3 (C—Ar), 169.9, 170.3 (CO).

Example 14

(S)-2-(3,5-dimethyl phenylacetamido)-3-phenyl-N-[4-(7-(2-morpholin-4-yl-ethoxy)imidazo[2,1-b]benzothiazol-2-yl)phenyl]propanamide (XXVI)

[General Formula (I) with m=1; p=r=0; R$_1$=[2-(morpholin-4-yl)-eth-7-oxy]; T=W1=W2=H; n=1; X=Ph; Y=CH$_2$-(3,5-Me)Ph]

yl]aniline and reagents as HATU and DIPHEA in dry DMF. The reaction mixture was stirred at room temperature for 6 h, at 70° C. for 48 h and at 155° C. for 24 h. Then the solvent was removed under reduced pressure and the crude mixture was purified by flash chromatography to give the desired product (S)-2-(3,5-dimethylphenylacetamido)-3-phenyl-N-[4-(7-(2-morpholin-4-yl-ethoxy)-imidazo[2,1-b]benzothiazol-2-yl)phenyl]propanamide Example 15

(S)-2-(3,5-bis(trifluoromethyl)phenylacetamido)-3-phenyl-N-[4-(7-(2-morpholin-4-yl-ethoxy)imidazo[2,1-b]benzothiazol-2-yl)phenyl]propanamide (XXVII)

[General Formula (I) with m=1; p=r=0; R$_1$=[2-(morpholin-4-yl)-eth-7-oxy]; T=W1=W2=H; n=1; X=Ph; Y=CH$_2$-(3,5-F$_3$C)Ph]

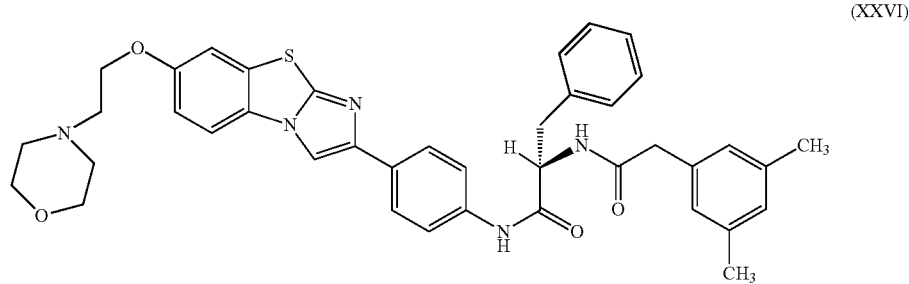

(XXVI)

Working as in the example 4, but using (S)-2-(2-(3,5-dimethylphenyl)acetamido)-3-phenyl-propionic acid and [4-(7-(2-morpholin-4-yl-ethoxy)imidazo[2,1-b]benzothiazol-2-

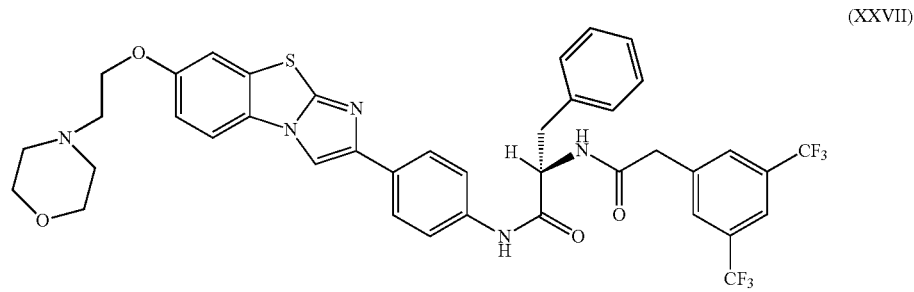 [SMILES: O=C(Cc1cc(C(F)(F)F)cc(C(F)(F)F)c1)N[C@@H](Cc1ccccc1)C(=O)Nc1ccc(-c2cn3c(n2)sc2cc(OCCN4CCOCC4)ccc23)cc1]

(XXVII)

Working as in the example 14, but using (S)-2-(2-(3,5-bis(trifluoromethyl)phenyl)acetamido)-3-phenyl-propionic acid the desired product (S)-2-(3,5-bis(trifluoromethyl)phenylacetamido)-3-phenyl-N-[4-(7-(2-morpholin-4-yl-ethoxy)-imidazo[2,1-b]benzothiazol-2-yl)phenyl]propanamide was recovered Example 16

(S)-2-(3,5-dimethyl phenylacetamido)-3-phenyl-N-[4-(6-(2-morpholin-4-yl-ethoxy)imidazo[2,1-b]benzothiazol-2-yl)phenyl]propanamide (XXVIII)

[General Formula (I) with m=1; p=r=0; $R_1$=[2-(morpholin-4-yl)-eth-6-oxy]; T=W1=W2=H; n=1; X=Ph; Y=$CH_2$-(3,5-Me)Ph]

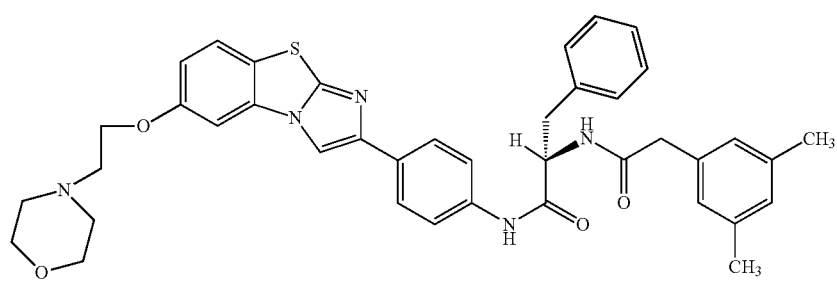

(XXVIII)

Working as in the example 14, but using 2-(4-aminophenyl)-6-(2-morpholin-4-yl-ethoxy)imidazo[2,1-b]-[1,3]benzothiazole, the desired product (S)-2-(3,5-dimethylphenyl acetamido)-3-phenyl-N-[4-(6-(2-morpholin-4-yl-ethoxy) imidazo[2,1-b]benzothiazol-2-yl)phenyl]propanamide was recovered.

Biological Results
Materials and Methods
Cell Culture

MDCK cells were grown in Dulbecco's modified Eagle's medium (DMEM) (Gibco BRL) containing 4 mM L-glutamine and supplemented with 2% (v/v) foetal bovine serum (Gibco BRL), 100 U/mL penicillin, and 100 µg/mL streptomycin. Cells were plated at a density of 1000 cells per well in 24-well microplates and allowed to settle overnight at 37° C. in a humidified atmosphere of 5% $CO_2$ prior to treatments. MCF10A human breast cells, MDA-MB231 human breast cancer cells, GTL-16 human gastric carcinoma cells, HepG2 human hepatocellular carcinoma cells, U-87 human glioblastoma-astrocytoma cells and LLC Lewis lung carcinoma cells were grown in RPMI medium (Gibco BRL) containing 4 mM L-glutamine and supplemented with 2% (v/v) foetal bovine serum (Gibco BRL), 100 U/mL penicillin, and 100 µg/mL streptomycin and kept at 37° C. in a humidified atmosphere of 5% $CO_2$.

Compound Treatments

For scattering assays, MDCK cells were pre-incubated with compounds for 2 hours at 0.1-100 µM concentrations at 37° C. in a humidified atmosphere of 5% CO2, followed by 24 hr stimulation with 20 ng/ml HGF (R&D Systems), as previously described (Patane et al., *Biochem Biophys Res Commun* 375, 184-189, 2008). The cells were further incubated at 37° C. in an atmosphere of 5% $CO_2$ for 24-48 hours, washed with phosphate-buffered saline (PBS; Gibco BRL), and fixed in PFA (Sigma). The quantification of scattering response was performed by counting the number of cells with scattered morphology in 30 independent colonies. The 1050 corresponds to the concentration of compounds leading to a 50% inhibition of Met-triggered cell scattering. Active compounds were assayed to impair scattering response also on human breast MCF10A cells following the same procedure. For survival assays, GTL-16, HepG2 and U-87 cells were cultured in serum-free media for 24 hours prior to compound addition for 48 hours. Viability was assessed with the Cell Titer Glo Luminescent Assay (Promega). For in vitro tumorigenesis, soft agar growth assays were preformed using GTL-16, HepG2, and U-87 cells, as previously described (Patane et al., *Cancer Res* 66, 4750-4757, 2006).

Biochemical Evaluation of Met Inhibitors

After starvation, cells were pretreated with inhibitors, then stimulated with HGF, and total extracts were analyzed as described (Maina et al., *Mol Cell* 7, 1293-1306, 2001). Antibodies used were anti-tubulin (Sigma), anti-phospho $Y_{1234-1235}$-Met, anti-Akt, anti-phospho-Akt, anti-phospho-Gab1, anti phosphor-ErbBs, anti-phospho-PDGFR, anti-PDGFRs, anti-ERKs (Cell Signaling), anti-ErbBs, anti-Met (Santa Cruz).

In Vivo Tumorigenesis Assays

Xenografts of GTL-16 cells were established by intraperitoneal (i.p.) or subcutaneously (into the flank/leg region) injection of cells ($10^6$) in nude mice (S/SOPF SWISS NU/NU; Charles River). Mice were then treated with the compound of example 4 (i.p. 30 mg kg-1) or vehicle every two days (GTL-16 cell intra-peritoneally injected at d=0, treatment started at d=1) or every day (GTL-16 cell intra-peritoneally injected at d=0, treatment started at d=7; GTL-16 cell subcutaneously injected at d=0, treatment started at d=1). Treatments were performed either one day or seven days after cancer cell injection. Mice were then sacrificed, and tumor nodule numbers present in the peritoneal cavity, the measure of their diameter and their total weight was evaluated. Three independent tumorigenesis assays were performed (8 mice per group were used).

Toxicity Evaluation of Compounds In Vivo

The weight of nude mice treated with the compound of example 4 (30 mg kg-1) or vehicle was measured before, during and after treatment. To evaluate the weight of heart, spleen, kidney, and liver, mice were sacrified after 21 days of treatment, organs were dissected, rinsed in PBS, and weight was measured.

Results

Identification of Compounds (I) as New Class of Met Inhibitor

Compounds were first submitted to a biological screening of cell motility, namely scattering response. MDCK epithelial cells acquire a "scattered phenotype" following stimulation by the Met ligand, HGF (Chan et al., *J Biomol Screen.* 13, 847-854, 2008; Corso et al., *Trends Mol Med* 11, 284-292, 2005; Patane et al., *Biochem Biophys Res Commun* 375, 184-189, 2008), allowing direct evaluation of compounds on Met functions. The Met inhibitor SU1127 was used as control in all assays (Schiering et al., *Proc Natl Acad Sci USA* 100, 12654-12659, 2003). Some results are reported in Table 1.

TABLE 1 scattering inhibition

| Compound | IC50 scattering inhibition | Toxicity |
|---|---|---|
| Example 1 (XIII) | 607 nM | >100 µM |
| Example 2 (XIV) | 559 nM | >100 µM |
| Example 4 (XVI) | 171 nM | >50 µM |
| Example 5 (XVII) | 206 nM | >50 µM |
| Example 6 (XVIII) | 760 nM | >100 µM |
| Reference compound (SU11274) | 251 nM | |

Compounds of examples 1 (XIII), 2 (XIV), 4 (XVI), 5 (XVII), and 6 (XVIII) in particular elicit inhibitory activity on Met-triggered cell scattering. The IC50 was calculated for the most active compounds (see Table 1). The SU11274 (Met inhibitor; Sugen) was used as reference compound. No toxic effects were observed at the doses used to impair Met-fucntions and only observed at higher concentrations (e.g. (XVI) started to be toxic at 100 µM; compounds XIII and XIV did not show toxicity at 300 µM). These findings were further supported by analysing the inhibitory activity of compounds on breast cells. We found that also in MCF10A cells, active compounds were able to impair Met-triggered scattering response at similar concentrations, without showing toxic effects. Altogether, these studies identify a new class of compounds of general formula (I), which are able to interfere with Met-triggered cell scattering.

Comparative Data

The test was conducted with the following compound comprising the scaffold disclosed by Patané et al., *Biochemical and Biophysical Research Communications* 375(2008) 184-189:

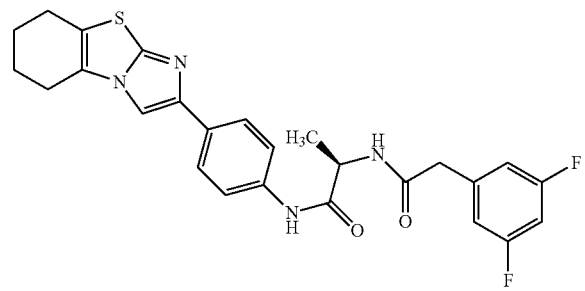 [SMILES: C[C@@H](NC(=O)Cc1cc(F)cc(F)c1)C(=O)Nc1ccc(-c2cn3c4c(sc3n2)CCCC4)cc1]

Said compound exhibited the following results:

| Scattering inhibition | Toxicity |
|---|---|
| 10 µM | at 100 µM |

These results show that the distinctive structural features of the compounds of the invention inexpectedly improve the activity and/or toxicity profiles.

Compounds of General Formula (I) Interfere with Met-Triggered Cell Survival In Vitro To assess whether the identified compounds prevent cell survival triggered by Met in vitro, we used GTL-16 cells. In this cell line, the met gene locus is amplified, resulting in expression of high levels of Met and its ligand independent activation. As consequences, GTL-16 cells become dependent on Met for survival, anchorage-independent growth, and tumour formation when injected in nude mice (Zou et al., *Cancer Res* 67, 4408-4417, 2007). We found that compounds (XIII) and (XVI) severely reduced Met-triggered anchorage-independent growth in a dose dependent manner. Similar results were obtained using HepG2 human hepatocellular carcinoma cells.

Thus, the compounds we have identified have the ability to interfere with in vitro cell survival triggered by the oncogenic Met.

Compounds of General Formula (I) Interfere with Met-Triggered Tumorigenesis In Vitro To ascertain whether the identified compounds prevent also Met-triggered tumorigenesis in vitro, we performed anchorage-independent growth assays, which is a hallmark of oncogenic transformation. Soft-agar growth of GTL-16 cells requires intact Met as it was impaired by the Met inhibitor SU11274 (Zou et al., 2007, supra). We found that compounds (XIII), (XVI) (aaa), and (aaa) severely affected Met-triggered anchorage-independent growth, in a dose dependent manner (FIG. 1). Similar results were obtained using HepG2 cells.

Data are summarized below:

| Compound | HepG2 IC 50 (nM) | GTL-16 (nM) |
|---|---|---|
| Example 4 (XVI) | 321 | 811 |
| Example 1 (XIII) | 2728 | 7725 |
| Example 1 (XVII) | | 1194 |
| Example 1 (XVIII) | | 5654 |

Thus, the compounds we have identified have the ability to interfere with in vitro tumorigenesis triggered by the oncogenic Met.

Figure 2:
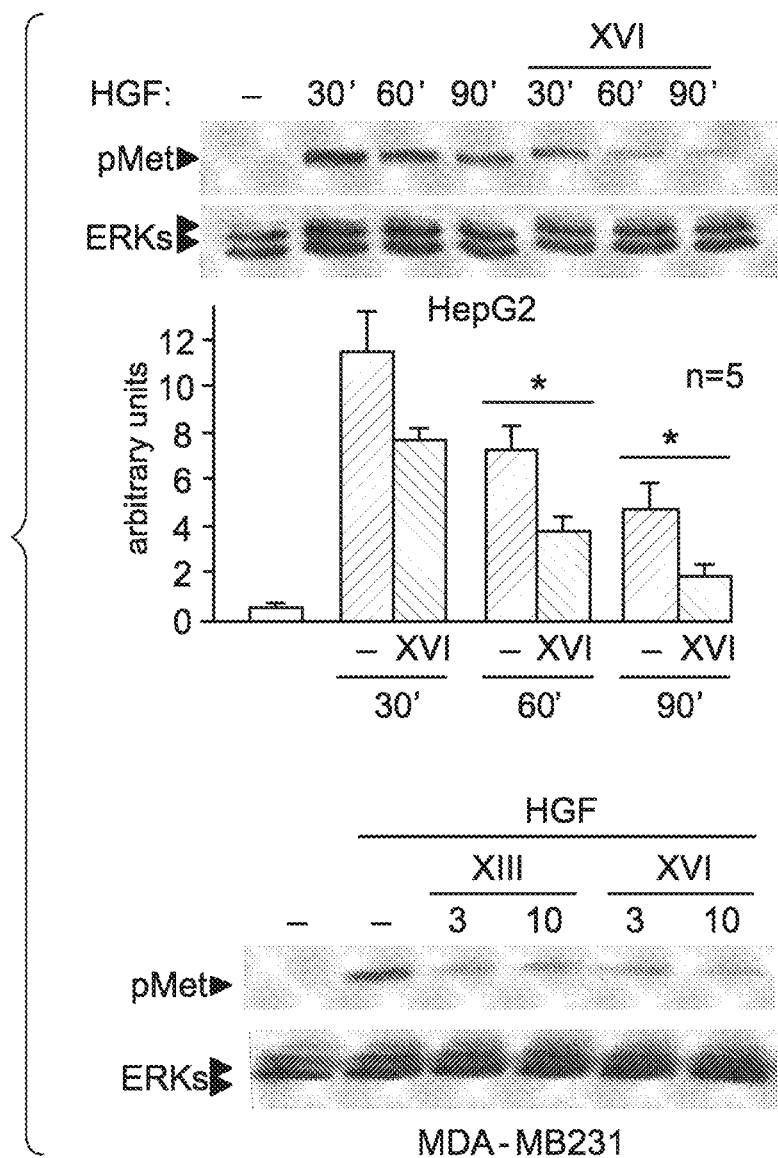
FIG. 2 illustrates the in vitro inhibition of Met phosphorylation by a compound of the invention on HepG2 cells and on human breast cancer MDA-MB231 cells (HGF 20 ng/ml).

Compounds of General Formula (I), affect Met Phosphorylation and Signalling in Living Cells Activation of Met by HGF can be biochemically evaluated by following its phosphorylation levels and activation of downstream targets. We started to biochemically characterise the inhibitory properties of identified compounds by following Met phosphorylation and its downstream targets in HepG2 cells. HepG2 cells showed high levels of Met phosphorylation upon HGF stimulation. In contrast, Met phosphorylation was significantly reduced by (XIII) and (XVI). These findings were further supported using other cell lines, such as MDA-MB231 human breast cancer cells (FIG. 2).

This event correlated with reduced downstream signals such as ERKs and Akt phosphorylation. Additional studies are currently in progress. These results suggest that the new scaffold we have identified act on Met to impair its signalling and biological functions.

Figure 3:
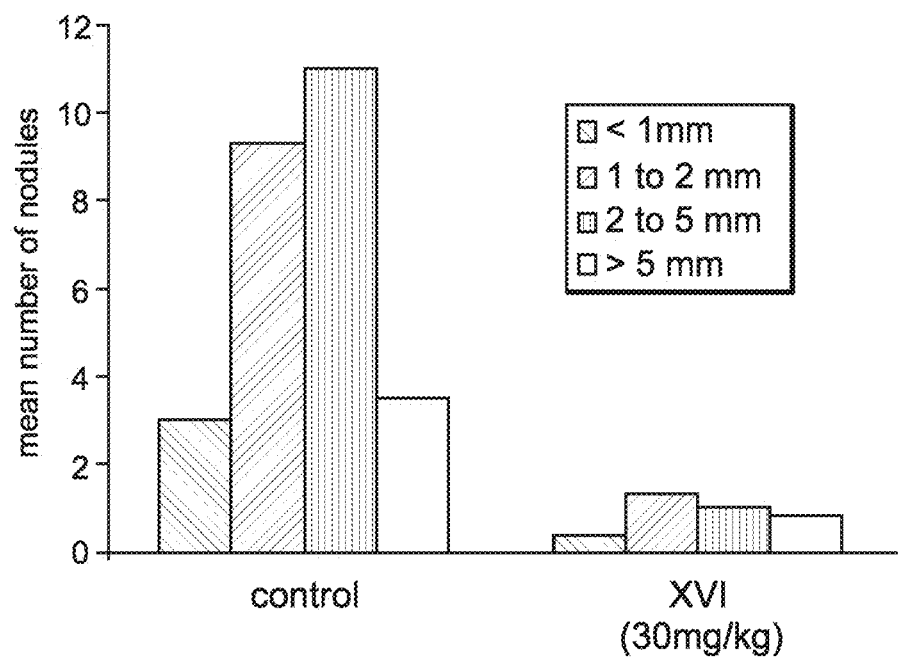
FIG. 3 illustrates the in vivo effect of the compound of example 4 on tumour growth following intra-peritoneal injection of GTL-16 cells in mice.

Compounds of General Formula (I), Interfere In Vivo with Tumour Growth of Cancer Cells Dependent on Oncogenic Met We evaluated the ability of compounds of general formula to impair tumour growth in vivo using nude mice injected intra-peritoneally with GTL-16 cells. Both the total weight and the number of tumours were drastically reduced in mice treated with the compound of example 4 (XVI). For example, when compounds were administered one day after intraperitoneally injection of GTL-16 cells, the mean numbers of nodules were the following: a) mice trated with vehicle: <1 mm: 3; 1-2 mm: 9.3; 2-5 mm: 11; >5 mm: 3.5. b) mice treated with the compound of example 4: <1 mm: 0.3; 1-2 mm: 1.3;

2-5 mm: 1; >5 mm: 0.8 (FIG. 3). Tumour growth was also reduced by approximately 30% when administration of compounds was performed seven days after GTL-16 cell intreperitoneally injection (data not shown). Moreover, tumour growth of GTL-16 cells subcutaneously injected was reduced by approximately 35% in mice treated with compounds (data not shown). Taken together, these findings provide evidence that the identified new scaffold interferes with tumour growth in vivo.

Compounds of General Formula (I), do not Show Major Toxic Effects In Vivo

We evaluated whether compounds of general formula elicited toxic effects in vivo by following mouse weight before, during and after treatment. No significant changes were observed in the weight of mice daily treated with the compound of example 4 (XVI; 30 mg kg-1) compared to those treated with the vehicle. We also evaluated the weight of heart, spleen, kidney and liver of mice treated with the compound of example 4 or vehicle. No differences were found between the two groups. Together, these findings show that the identified new scaffold is well tolerated when injected in mice at the dose required to interfere with tumour growth.

Compounds of General Formula (I), Restrain Phosphorylation and Function of other Signalling Targets We evaluated whether compounds of general formula elicited inhibitory effects on other signalling targets using cancer cells with different oncogenic signals. Reduced phosphorylation of full-length and truncated forms of Ron was observed. This was accompanied with reduced proliferation of cells with oncogenic Ron, accompanied with an increase of cell death. Reduced phosphorylation of other signals, such as component of the Pl3K pathway (e.g. Akt) or PDGFR was also observed. This was accompanied by reduced anchorage-independent growth of cells with oncogenic Met, PDGFR and ErbBs. Additional studies are currently in progress.

NCI60 Assays

Compound of example 4 was screened in the NCI 60 human tumour cell line anticancer drug screen (Shoemaker et al *Nature reviews* 6, 2006, 813-823). Results are summarized in the table below:

| Panel/Cell line | Growth Percent (conc. $10^{-5}$M) |
|---|---|
| Leukemia | |
| CCRF-CEM | 32.94 |
| HL-60(TB) | 79.95 |
| K-562 | 63.10 |
| MOLT-4 | 43.46 |
| RPMI -8226 | 66.73 |
| SR | 58.33 |
| Non-Small Cell Lung Cancer | |
| A549/ATCC | 31.71 |
| EKVX | 15.48 |
| HOP-62 | 80.02 |
| HOP-92 | 71.89 |
| NCI•H226 | 90.93 |
| NCI-H23 | 39.55 |
| NCI-H322M | 28.70 |
| NCI-H460 | −16.59 |
| Colon Cancer | |
| COLO 205 | 71.04 |
| HCC-2998 | 98.28 |
| HCT-116 | 21.40 |
| HCT-15 | 44.16 |
| HT29 | 18.28 |
| KM12 | 16.15 |
| SW-620 | 12.13 |

-continued

| Panel/Cell line | Growth Percent (conc. $10^{-5}$M) |
|---|---|
| CNS Cancer | |
| SF-268 | 29.28 |
| SF-295 | 42.18 |
| SF-539 | 36.76 |
| SNB-19 | 69.84 |
| SNB-75 | 20.69 |
| U251 | 34.24 |
| Melanoma | |
| LOX IMVI | 26.60 |
| M14 | 30.58 |
| MDA-MB-435 | 54.92 |
| SK-MEL-2 | 45.85 |
| SK-MEL-28 | 26.28 |
| SK-MEL-5 | 10.83 |
| UACC-257 | 55.20 |
| UACC-62 | 69.45 |
| Ovarian Cancer | |
| IGROV 1 | 13.32 |
| OVCAR-3 | 2.50 |
| OVCAR-4 | −0.79 |
| OVCAR-5 | 97.36 |
| OVCAR-8 | 3.54 |
| NCI/ADR-RES | 43.07 |
| SK-OV-3 | 96.62 |
| Renal Cancer | |
| 786-0 | 60.35 |
| A498 | 120.10 |
| ACHN | 81.23 |
| CAK I-1 | 53.37 |
| RXF 393 | 47.02 |
| SN12C | 47.40 |
| TK-10 | 61.11 |
| UO-31 | 67.05 |
| Prostate Cancer | |
| PC-3 | 38.29 |
| DU-145 | 70.37 |
| Breast Cancer | |
| MCF7 | 59.09 |
| MDA-MB-231/ATCC | 17.15 |
| HS 578T | 16.75 |
| BT-549 | 82.05 |
| T-47D | 67.66 |
| MDA-MB-468 | 78.09 |

These results show that the compounds of the invention: 1) selectively act on specific oncogenic pathways to which cancer cells are dependent/addicted; 2) may be therapeutically used for several type of tumours; 3) do not elicit, per se, unspecific effects on cells, further strengthening their low toxic properties.

Cyclodextrin Encapsulation

Materials and Methods

Preparation of β-Cyclodextrin/Compound Mixture (β-CD/(XVI), Referred to as (XXIX))

To an aqueous solution containing 37.5 mg of β-cyclodextrin (β-CD) in 2.5 ml water at approximately 60° C., 20 mg of compound (XVI), prepared according to example 4, was added and the mixture was slowly cooled at room temperature, filtered and the precipitate washed with 20 ml of water. The mother liquors and washing were concentrated at reduced pressure to afford a white solid mixture (XXIX). HPLC analysis revealed that (XXIX) contained 10% of compound (XVI), as determined by HPLC analysis. Mixture (XXIX) was then biologically evaluated by performing scattering assays as previously described.

Results

Compounds of General Formula (I), Elicit Effective Inhibitory Effects when Mixed with β-Cyclodextrin The inhibitory effects of mixture (XXIX) (β-CD/(XVI) mixture) were evaluated by comparing the ability of compounds (XXIX) with (XVI) to impair Met-triggered scattering response. We found that mixture (XXIX) elicited inhibitory effects at concentrations approximately 10 folds lover that those required when (XVI) compound was not mixed with β-CD. These results indicate that encapsulation strategies may increase the effectiveness of the identified compounds.

The invention claimed is:

1. Compounds of formula (I):

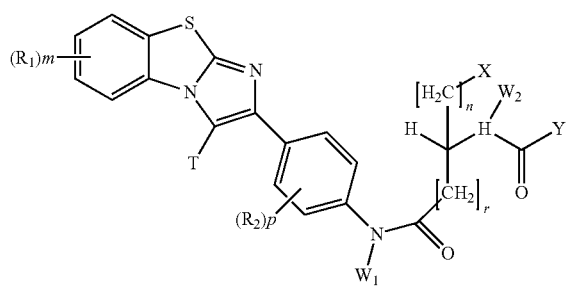

wherein:
- m is an integer chosen from 0, 1, 2, 3 and 4;
- p is an integer chosen from 0, 1, 2, 3 and 4;
- each R1, identical or different, is independently chosen from halogen atoms or a group chosen from alkyl, cycloalkyl, COOR, perhalogenoalkyl, CN, NRR', aryl, heteroaryl, -alkylaryl, -alkylheterocyclyl, $S(O)_q R$, OH or Oalkyl where alkyl is optionally substituted with one or more of identical or different substituents independently chosen from halogen atoms, OR, NRR' or non aromatic heterocycle;
- each R2, identical or different, is independently chosen from halogen atoms, alkyl, cycloalkyl, COOR, perhalogenoalkyl, CN, NRR', aryl, heteroaryl, -alkylaryl, -alkylheterocyclyl, $S(O)_q R$, OHor Oalkyl where alkyl is optionally substituted with one or more of identical or different substituents independently chosen from halogen atoms, OR or NRR';
- T is a hydrogen or a halogen atom;
- n is an integer chosen from 0, 1 and 2, where, when n is 0, the carbon atom is absent;
- r is an integer chosen from 0 and 1, where, when r is 0, the carbon atom is absent;
- $W_1$ is a hydrogen atom or an alkyl, aryl or -alkylaryl;
- $W_2$ is a hydrogen atom or an alkyl or -alkylaryl;
- X is an aryl, -alkylaryl or heteroaryl, each being optionally substituted by one or more identical or different groups, independently chosen from OR, COOR, NRR', halogen atom, $S(O)_q R$, alkyl, aryl, CN, or perhalogenoalkyl;
- Y is an alkyl, cycloalkyl, aryl, -alkylaryl, -alkylheteroaryl or heteroaryl, each being optionally substituted by one or more identical or different substituents independently chosen from halogen atom, OR, COOR, NRR', CN, $S(O)_q R$, alkyl, aryl or perhalogenoalkyl;
- q is an integer chosen from 0, 1 or 2;
- R and R', identical or different, independently represent a H atom, alkyl, aryl, or -alkylaryl or R and R' together form with the N atom to which they are attached a heteroaryl or heterocyclic ring;

wherein, unless specified, the alkyl, aryl, -alkylaryl, heteroaryl, or heterocyclic ring are optionally substituted by one or more of halogen atom, OH, COOR, (O)lkyl, OAryl, OAlkylaryl, $NH_2$, NHAlkyl, $NAlkyl_2$, $NAryl_2$, NHAryl, NHAlkylaryl, $NAlkylaryl_2$, N(Alkyl)alkylaryl, CN, perhalogenoalkyl, SH, SAlkyl, SOAlkyl, $SO_2$alkyl, aryl or alkylaryl;

either as racemic mixtures or pure or enantioenriched enantiomers, and pharmaceutically acceptable salts thereof.

2. The compounds according to claim 1 in which m=0 or 1, p=0, r=0 and T=H.

3. The compounds according to claim 1 of formula (Ia):

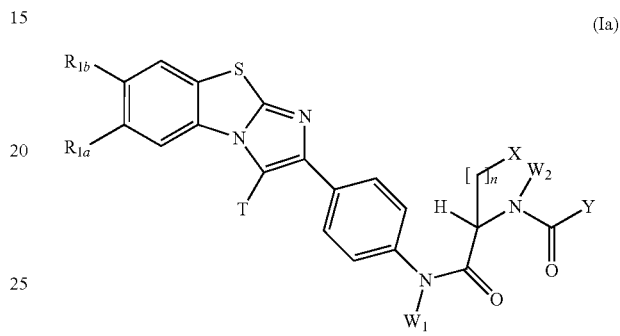

wherein:
- $R_{1a}$ and $R_{1b}$ identical or different are independently chosen from hydrogen or halogen atoms or a group chosen from perhalogenoalkyl, CN, NRR', aryl, alkyl, OH or Oalkyl where alkyl is optionally substituted with one or more identical or different substituents independently chosen from halogen atom, OR, NRR' or non aromatic heterocycle, such as morpholinyl;
- T is a hydrogen or a halogen atom;
- n is an integer chosen from 0 and 1, where, when n is 0, the carbon atom is absent;
- $W_1$ and $W_2$, identical or different, are chosen from a hydrogen atom or a $C_{1-4}$ alkyl;
- X is an aryl or heteroaryl, each being optionally substituted by one or more identical or different groups, independently chosen from OR, COOR, NRR', halogen atom, $S(O)_q R$, alkyl, aryl, CN or perhalogenoalkyl;
- Y is an alkyl, aryl, -alkylaryl such as —$CH_2$aryl or heteroaryl, each being optionally substituted by one or more identical or different substituents independently chosen from halogen atom, OR, COOR, NRR', CN, $S(O)_q R$, alkyl, aryl or perhalogenoalkyl;
- q is an integer chosen from 0, 1 or 2;
- R and R', identical or different, independently represent a hydrogen atom, alkyl, aryl, or alkylaryl or R and R' together form with the N atom to which they are attached a heterocyclic ring;
  - wherein the alkyl, aryl, -alkylaryl, or heterocyclic ring are optionally substituted by one or more of halogen atom, OH, (O)lkyl, OAryl, OAlkylaryl, $NH_2$, NHAlkyl, $NAlkyl_2$, NHAryl, $NAryl_2$, NHAlkylaryl, NAlkylaryl, $NAlkylaryl_2$, N(Alkyl)alkylaryl, CN, perhalogenoalkyl, SH, SAlkyl, SOAlkyl, $SO_2$alkyl, aryl or alkylaryl;

either as racemic mixture or pure or enantioenriched enantiomers, as well as the pharmaceutically acceptable salts thereof.

4. The compounds according to claim 1, in which $W_1=W_2=H$.

5. The compounds according to claim 1, in which n=0 or 1 and X is an optionally substituted aryl or heteroaryl.

6. The compounds according to claim 1, in which X is phenyl.

7. The compounds according to claim 1, in which Y is an -alkylaryl, such as —CH$_2$aryl, where the aryl is optionally substituted by one or more identical or different substituents chosen from halogen, OR, NRR', SR, alkyl, CN or perhalogenoalkyl.

8. The compounds according to claim 1 chosen from:
2-(3,5-dimethylphenylacetamido)-3-phenyl-N-[4-(imidazo[2,1-b]benzothiazol-2-yl)phenyl]propanamide;
2-(3,5-dimethylphenylacetamido)-3-(4-hydroxyphenyl)-N-[4-(imidazo[2,1-b]benzo thiazol-2-yl)phenyl]propanamide;
2[(3,5-bis(trifluoromethyl)phenylacetamido)-3-phenyl-N-[4-(imidazo[2,1-b]benzo thiazol-2-yl)phenyl]propanamide;
2[(3,5-difluorophenylacetamido)-3-phenyl-N-[4-(imidazo[2,1-b]benzothiazol-2-yl)phenyl]propanamide;
2-(3,5-dimethylphenylacetamido)-3-(3-indolyl)-N-[4-(imidazo[2,1-b]benzothiazol-2-yl)phenyl]propanamide;
2-[(3,5-bis(trifluoromethyl)phenylacetamido)-3-(3-indolyl)-N-[4-(imidazo[2,1-b]benzothiazol-2-yl)phenyl]propanamide;
2-[(3,5-bis(trifluoromethyl)phenylacetamido)-3-(2-naphthyl)-N-[4-(imidazo[2,1-b]benzothiazol-2-yl)phenyl]propanamide;
2-(3,5-dimethylphenylacetamido)-3-(2-naphtyl)-N-[4-(imidazo[2,1-b]benzothiazol-2-yl)phenyl]propanamide;
2[(3,5-bis(trifluoromethyl)phenylacetamido)-3-phenyl-N-[4-(imidazo[2,1-b](6-methoxy)benzo thiazol-2-yl)phenyl]propanamide;
2[(3,5-bis(trifluoromethyl)phenylacetamido)-3-phenyl-N-[4-(imidazo[2,1-b](6-(3-(dimethylamino)propoxy)benzo thiazol-2-yl)phenyl]propanamide;
2[(3,5-bis(trifluoromethyl)phenylacetamido)-3-phenyl-N-[4-(imidazo[2,1-b](6-(3-(hydroxy)propoxy)benzo thiazol-2-yl)phenyl]propanamide;
(S)-2-(3,5-bis(trifluoromethyl)phenylacetamido)-3-phenyl-N-[4-(7-bromo)imidazo[2,1-b]benzothiazol-2-yl)phenyl]propanamide;
(S)-2-(4-methylphenylacetamido)-3-phenyl-N-[4-(imidazo[2,1-b]benzothiazol-2-yl)phenyl]propanamide;
(S)-2-(3,5-dimethyl)phenylacetamido)-3-(4-methylphenyl)-N-[4-(imidazo[2,1-b]benzothiazol-2-yl)phenyl]propanamide;
(S)-2-(3,5-bis(trifluoromethyl)phenylacetamido)-3-(4-methylphenyl)-N-[4-(imidazo[2,1-b]benzothiazol-2-yl)phenyl]propanamide;
(S)-2-(3,5-dimethylphenylacetamido)-3-(1H-indol-3-yl)-N-[4-(imidazo[2,1-b]benzothiazol-2-yl)phenyl]propanamide;
(S)-2-(3,5-bis(trifluoromethylphenylacetamido)-3-(1H-indol-3-yl)-N-[4-(imidazo[2,1-b]benzothiazol-2-yl)phenyl]propanamide;
(S)-2-(3,5-dimethylphenylacetamido)-3-phenyl-N-[4-(7-(2-morpholin-4-yl-ethoxy)imidazo[2,1-b]benzothiazol-2-yl)phenyl]propanamide;
(S)-2-(3,5-bis(trifluoromethyl)phenylacetamido)-3-phenyl-N-[4-(7-(2-morpholin-4-yl-ethoxy)imidazo[2,1-b]benzothiazol-2-yl)phenyl]propanamide or
(S)-2-(3,5-dimethylphenylacetamido)-3-phenyl-N-[4-(6-(2-morpholin-4-yl-ethoxy)imidazo[2,1-b]benzothiazol-2-yl)phenyl]propanamide or their racemic mixtures or pure or enantioenriched enantiomers, and pharmaceutically acceptable salts thereof.

9. The compounds according to claim 1 chosen from:
(S)-2-(3,5-dimethylphenylacetamido)-3-phenyl-N-[4-(imidazo[2,1-b]benzothiazol-2-yl)phenyl]propanamide;
(R)-2-(3,5-dimethylphenylacetamido)-3-phenyl-N-[4-(imidazo[2,1-b]benzothiazol-2-yl)phenyl]propanamide;
(S)-2[(3,5-bis(trifluoromethyl)phenylacetamido)-3-phenyl-N-[4-(imidazo[2,1-b]benzothiazol-2-yl)phenyl]propanamide;
(R)-2[(3,5-bis(trifluoromethyl)phenylacetamido)-3-phenyl-N-[4-(imidazo[2,1-b]benzothiazol-2-yl)phenyl]propanamide;
(S)-2[(3,5-difluorophenylacetamido)-3-phenyl-N-[4-(imidazo[2,1-b]benzothiazol-2-yl)phenyl]propanamide;
(R)-2[(3,5-difluorophenylacetamido)-3-phenyl-N-[4-(imidazo[2,1-b]benzothiazol-2-yl)phenyl]propanamide;
(S)-2-(3,5-bis(trifluoromethyl)phenylacetamido)-3-phenyl-N-[4-(7-bromo)imidazo[2,1-b]benzothiazol-2-yl)phenyl]propanamide or
(S)-2-(4-methylphenylacetamido)-3-phenyl-N-[4-(imidazo[2,1-b]benzothiazol-2-yl)phenyl]propanamide as well as their pharmaceutically acceptable salts.

10. A process of preparation of a compound of formula (I) according to claim 1, comprising the step of reacting a corresponding compound of formula (II) with a corresponding compound of formula (III), or precursors thereof:

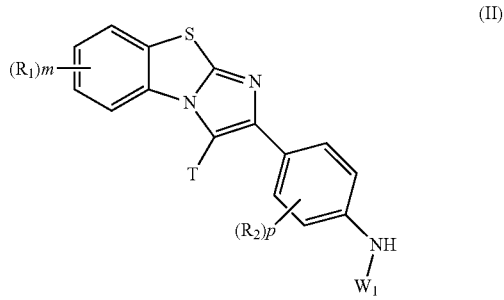

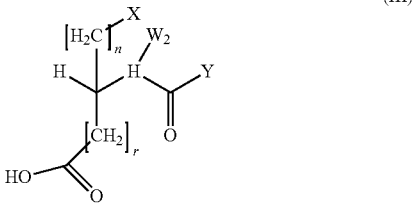

wherein $R_1$, $R_2$, T, W, $W_1$, $W_2$, X, Y, m, n, p, and r are as defined in claim 1.

11. A process of preparation of a compound (I) according to claim 1 comprising the step of reacting a corresponding compound of formula (IV) with a corresponding compound of formula (V), or precursors thereof:

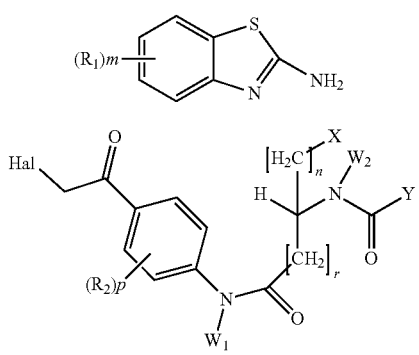

(IV)

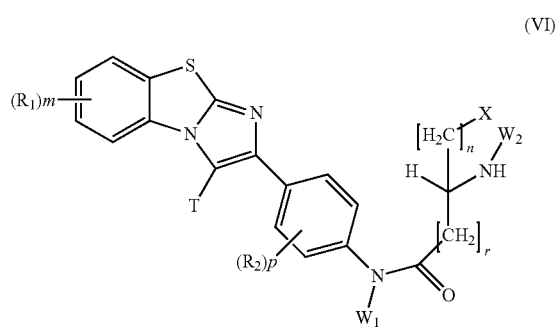

(V)

wherein
R₁, R₂, T, W, W₁, W₂, X, Y, m, n, p, and r are as defined in claim 1 and Hal represents a halogen atom.

12. A process of preparation of a compound (I) according to claim 1 comprising reacting a corresponding compound of formula (VI) with a corresponding compound of formula (VII), or precursors thereof:

(VI)

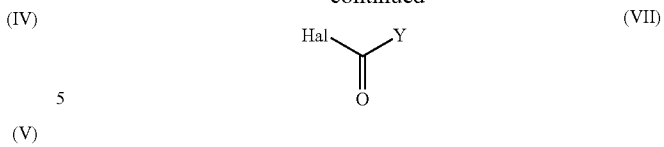

(VII)

wherein
R₁, R₂, T, W, W₁, W₂, X, Y, m, n, p, and r are as defined in claim 1 and Hal represents a halogen atom.

13. The process according to claim 10, further comprising the step of isolating the obtained compound.

14. A pharmaceutical composition comprising a compound of formula (I) as defined in claim 1 and a pharmaceutically acceptable carrier.

15. The composition according to claim 14 where said carrier is a cyclodextrin.

16. A method for inhibiting the Met family comprising administering to a person in need thereof a compound of formula (I) as defined in claim 1.

17. A method for treating pain, leukemia, non-small cell lung cancer, colon cancer, melanoma, ovarian cancer, renal cancer, prostate cancer and breast cancer comprising administering to a person in need thereof a compound of formula (I) as defined in claim 1.

18. A method for treating pain, leukemia, non-small cell lung cancer, colon cancer, melanoma, ovarian cancer, renal cancer, prostate cancer and breast cancer comprising administering, to a person in need thereof, a combination of a compound as defined in claim 1 with one or more agent(s) and/or pharmaceutical composition(s).

19. A method for treating distinct tumors from leukemia, non-small cell lung cancer, colon cancer, melanoma, ovarian cancer, renal cancer, prostate cancer and breast cancer characterized by alteration of selective signals comprising administering a compound of formula (I), to a person in need thereof, as defined in claim 1.

\* \* \* \* \*